United States Patent
Murakami et al.

(10) Patent No.: US 10,189,804 B2
(45) Date of Patent: Jan. 29, 2019

(54) METHOD FOR PRODUCING DICARBOXYLIC ACID COMPOUND

(71) Applicant: DAIICHI SANKYO COMPANY, LIMITED, Tokyo (JP)

(72) Inventors: Masayuki Murakami, Hiratsuka (JP); Yuichi Aki, Hiratsuka (JP); Daisuke Fukatsu, Hiratsuka (JP); Kenichi Kimura, Hiratsuka (JP); Makoto Michida, Hiratsuka (JP); Koji Hamaoka, Hiratsuka (JP)

(73) Assignee: DAIICHI SANKYO COMPANY, LIMITED, Tokyo (JP)

( * ) Notice: Subject to any disclaimer, the term of this patent is extended or adjusted under 35 U.S.C. 154(b) by 0 days.

(21) Appl. No.: 15/568,691

(22) PCT Filed: Apr. 22, 2016

(86) PCT No.: PCT/JP2016/062717
§ 371 (c)(1),
(2) Date: Oct. 23, 2017

(87) PCT Pub. No.: WO2016/171240
PCT Pub. Date: Oct. 27, 2016

(65) Prior Publication Data
US 2018/0148424 A1    May 31, 2018

(30) Foreign Application Priority Data

Apr. 24, 2015 (JP) ................. 2015-088932

(51) Int. Cl.
| | | |
|---|---|---|
| *C07D 295/155* | (2006.01) | |
| *C07D 227/04* | (2006.01) | |
| *C07C 227/04* | (2006.01) | |
| *C07C 227/42* | (2006.01) | |
| *C07C 229/48* | (2006.01) | |
| *C07C 229/52* | (2006.01) | |
| *C07D 295/14* | (2006.01) | |
| *C07C 205/57* | (2006.01) | |

(Continued)

(52) U.S. Cl.
CPC ........ *C07D 295/155* (2013.01); *C07C 205/57* (2013.01); *C07C 227/04* (2013.01); *C07C 227/06* (2013.01); *C07C 227/10* (2013.01); *C07C 227/36* (2013.01); *C07C 227/42* (2013.01); *C07C 229/48* (2013.01); *C07C 229/52* (2013.01); *C07D 227/04* (2013.01); *C07D 295/14* (2013.01); *A61K 31/4453* (2013.01); *C07B 61/00* (2013.01); *C07C 227/08* (2013.01); *C07C 2601/14* (2017.05)

(58) Field of Classification Search
CPC .................................................. C07D 295/155
USPC ...................................................... 546/234
See application file for complete search history.

(56) References Cited

U.S. PATENT DOCUMENTS 8,426,429 B2 * 4/2013 Baxter ............... C07D 215/227
                                                    514/231.5
9,617,232 B2 * 4/2017 Uto ....................... C07D 213/75
(Continued)

FOREIGN PATENT DOCUMENTS

| JP | 4389683 | 12/2009 |
| JP | 2013-095703 | 5/2013 |

(Continued)

OTHER PUBLICATIONS

Montalbetti, Tetrahedron 61 (2005) 10827-10852.*
(Continued)

*Primary Examiner* — Nizal S Chandrakumar
(74) *Attorney, Agent, or Firm* — Foley & Lardner LLP

(57) ABSTRACT

It is an object of the present invention to provide an excellent method for producing an excellent therapeutic agent.
The solution of the present invention is as shown in the following scheme:

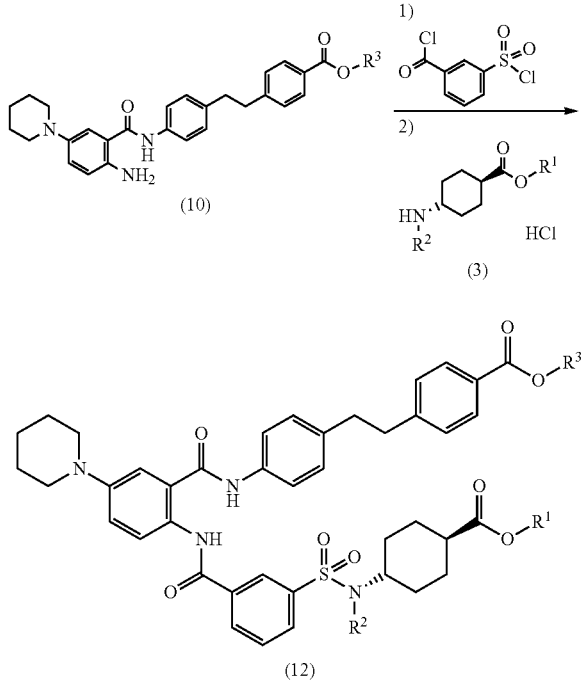

wherein $R^1$ represents a C1-C6 alkyl group, $R^2$ represents a C1-C6 alkyl group, and $R^3$ represents a C1-C6 alkyl group.

15 Claims, No Drawings

(51) Int. Cl.
  *C07C 227/06*   (2006.01)
  *C07C 227/10*   (2006.01)
  *C07C 227/36*   (2006.01)
  *A61K 31/4453*  (2006.01)
  *C07B 61/00*    (2006.01)
  *C07C 227/08*   (2006.01)

(56) References Cited

U.S. PATENT DOCUMENTS

| 9,670,173 B2 * | 6/2017 | Uto ................... C07D 213/75 |
| 2009/0253719 A1 * | 10/2009 | Pimplaskar ......... A61K 31/517 |
| | | 514/266.4 |
| 2013/0029973 A1 | 1/2013 | Hachiya et al. |

FOREIGN PATENT DOCUMENTS

| JP | WO 2014175317 | * 10/2014 | ........... C07C 311/20 |
| WO | WO-2007/073934 | 7/2007 | |
| WO | WO-2013/062065 | 5/2013 | |
| WO | WO-2014/003153 | 1/2014 | |
| WO | WO-2014/175317 | 10/2014 | |

OTHER PUBLICATIONS

Supplementary European Search Report dated Aug. 17, 2018 in corresponding application 16783261.
Wall et al, Variation of Formal Hydrogen-Bonding Networks within Electronically Delocalized Conjugated Oligopeptide Nanostructures,Langmuir,2014, vol. 30, pp. 11375-11385.

* cited by examiner

METHOD FOR PRODUCING DICARBOXYLIC ACID COMPOUND

CROSS-REFERENCE TO RELATED APPLICATIONS

The present application is a U.S. national stage application of International Patent Application No. PCT/JP2016/062717, filed Apr. 22, 2016, which claims the benefit of priority to Japanese Patent Application No. 2015-088932, filed Apr. 24, 2015, the entireties of which are incorporated herein by reference.

TECHNICAL FIELD

The present invention relates to a method for efficiently producing a dicarboxylic acid compound, and a high-purity dicarboxylic acid compound can be produced highly efficiently at low cost.

BACKGROUND ART

To date, a compound that is useful for prevention or treatment of hyperphosphatemia or hyperphosphatemia-related diseases, or a pharmacologically acceptable salt thereof, has been known. Examples of such a compound include the following compounds disclosed in WO2014/175317 (Patent Literature 1), and pharmacologically acceptable salts thereof.

[Formula 1]

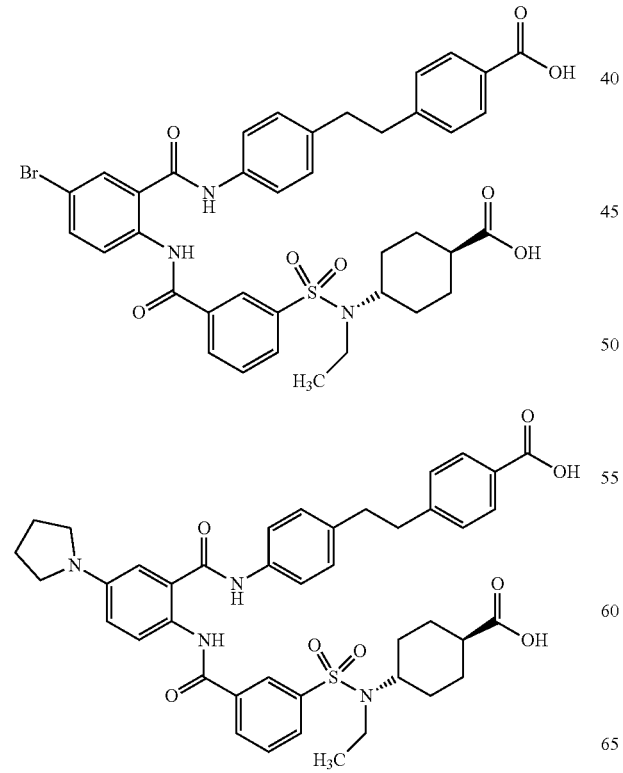

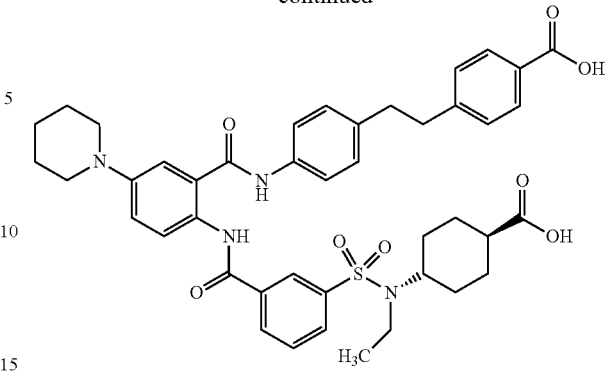

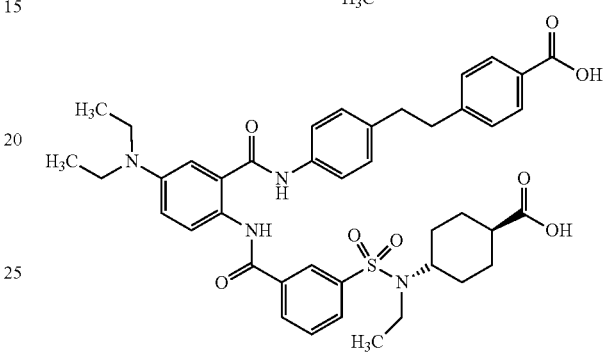

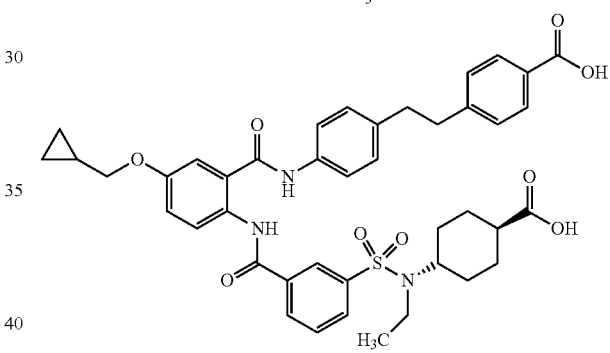

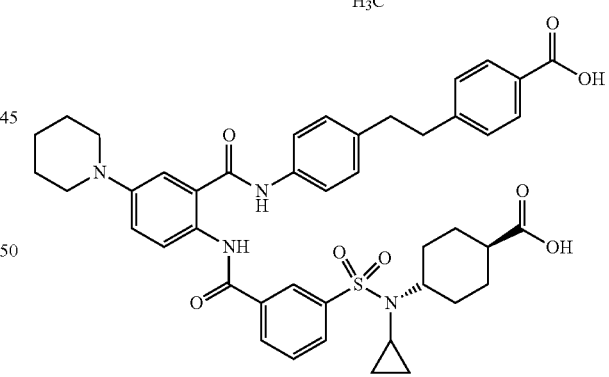

CITATION LIST

Patent Literature

Patent Literature 1: WO2014/175317
Patent Literature 2: Japanese Patent No. 4389683
Patent Literature 3: WO2013/062065
Patent Literature 4: WO2014/003153
Patent Literature 5: WO2000/7073934
Patent Literature 6: Japanese Patent Laid-Open No. 2013-95703
Patent Literature 7: Japanese Patent No. 4389683

SUMMARY OF INVENTION

Technical Problem

From an industrial viewpoint, the method for producing a dicarboxylic acid compound disclosed in Patent Literature 1 is not necessarily an efficient production method. Also, in terms of yield and operability, the production method has needed to be improved. Thus, the present inventors have continuously conducted intensive studies, thereby completing the present invention.

Solution to Problem

The present invention will be described below.

[1]

A method for producing a compound represented by formula (13) or a pharmacologically acceptable salt thereof, the method comprising:

(i) a step of
1) reacting a compound represented by formula (10) or a compound represented by formula (11) with 3-(chlorosulfonyl)benzoyl chloride in a solvent to obtain a condensate, and then 2) reacting the condensate with a compound represented by formula (3) in a solvent in the presence of a base to produce a compound represented by formula (12):

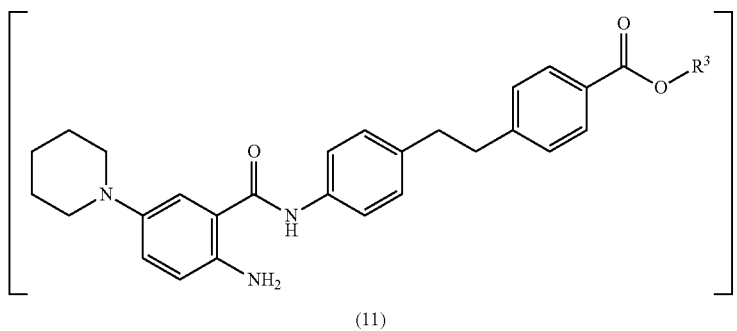

(10)

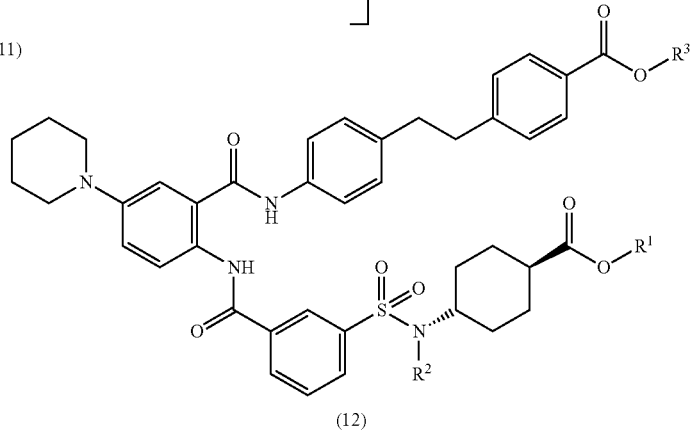

(11)

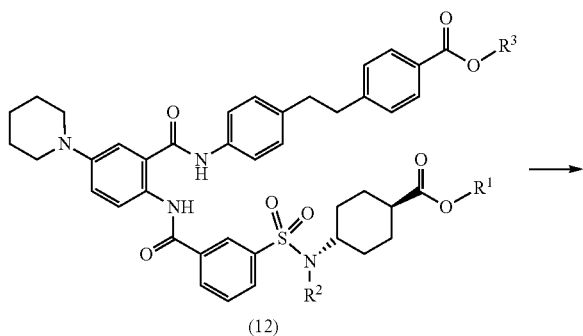

wherein $R^1$ represents a C1-C6 alkyl group, $R^2$ represents a C1-C6 alkyl group, $R^3$ represents a C1-C6 alkyl group, and HX represents an acid; and (ii) a step of subjecting the compound represented by formula (12) produced in the previous step to a hydrolysis reaction in the presence of aqueous alkali in a solvent to produce a compound represented by formula (13):

[Formula 3]

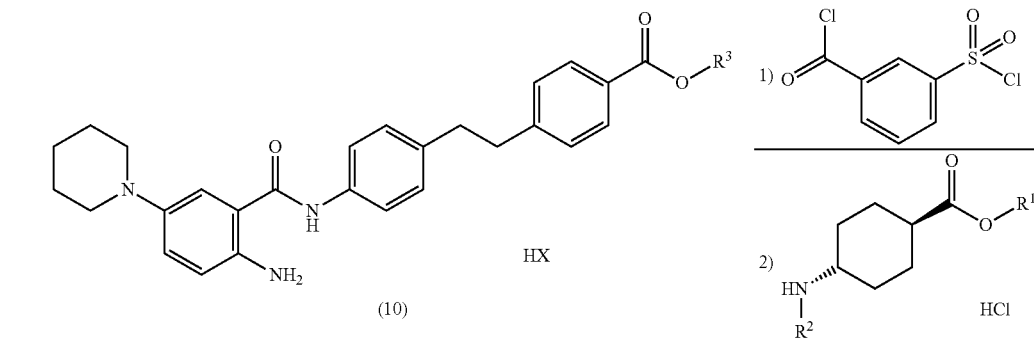

(12)

[Formula 2]

5

-continued

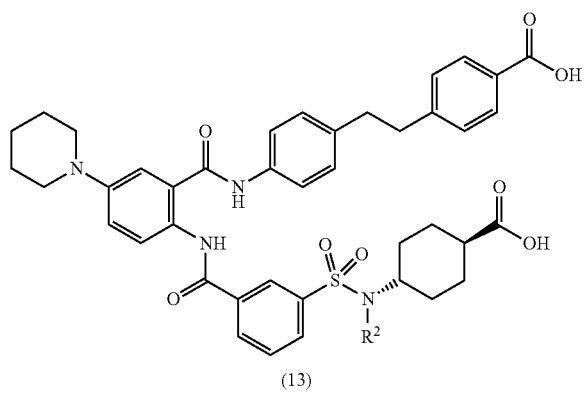

(13)

wherein $R^1$ represents a C1-C6 alkyl group, $R^2$ represents a C1-C6 alkyl group, and $R^3$ represents a C1-C6 alkyl group.

[2]

The method according to [1] above, wherein in the step (i), 1), the solvent is N,N-dimethylacetamide, acetonitrile or acetonitrile-tetrahydrofuran; in the step (i), 2), the solvent is N,N-dimethylacetamide, tetrahydrofuran or acetonitrile-tetrahydrofuran, and the base is triethylamine, diethylisopropylamine, N-methylmorpholine, dimethylbenzylamine or cesium carbonate; and further a small amount of trimethylsilyl chloride is added.

[3]

The method according to [1] or [2] above, wherein in the step (ii), the aqueous alkali is an aqueous sodium hydroxide solution, and the solvent is N,N-dimethylacetamide, methanol-tetrahydrofuran (volume ratio: 1:0.5-2) or methanol-acetonitrile (volume ratio: 1:0.5-2).

[4]

A method for producing a compound represented by formula (10) or a compound represented by formula (11) used in the method according to any one selected from [1] to [3] above, the method comprising:

(i) a step of subjecting a compound represented by formula (6) to a condensation reaction with 5-chloro-2-nitrobenzoyl chloride in a solvent in the presence of a base to produce a compound represented by formula (8):

[Formula 4]

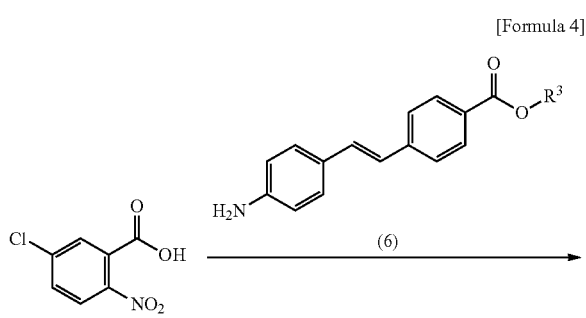

6

-continued

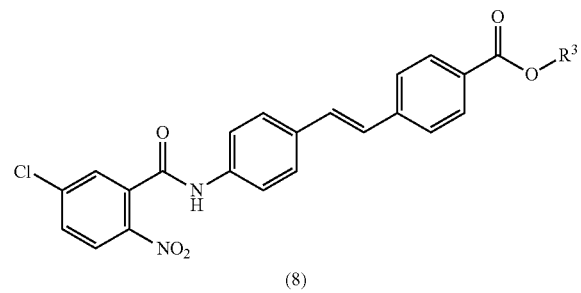

(8)

wherein $R^3$ represents a C1-C6 alkyl group;

(iii) a step of reacting the compound represented by formula (8) produced in the previous step with piperidine in a solvent to produce a compound represented by formula (9):

[Formula 6]

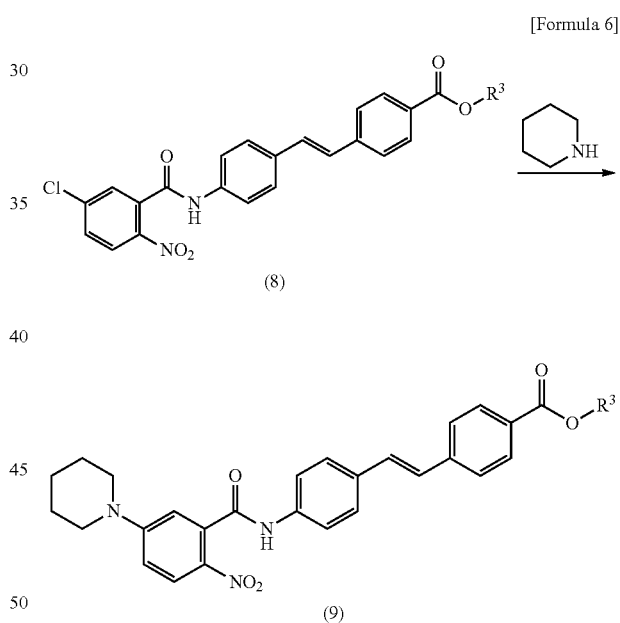

wherein $R^3$ represents a C1-C6 alkyl group; and (iii) a step of treating the compound represented by formula (9) produced in the previous step with an acid in a solvent in the presence of a catalyst under a hydrogen atmosphere to produce a compound represented by formula (10); or a step of treating the compound represented by formula (9) produced in the previous step in a solvent in the presence of a catalyst under a hydrogen atmosphere to produce a compound represented by formula (11):

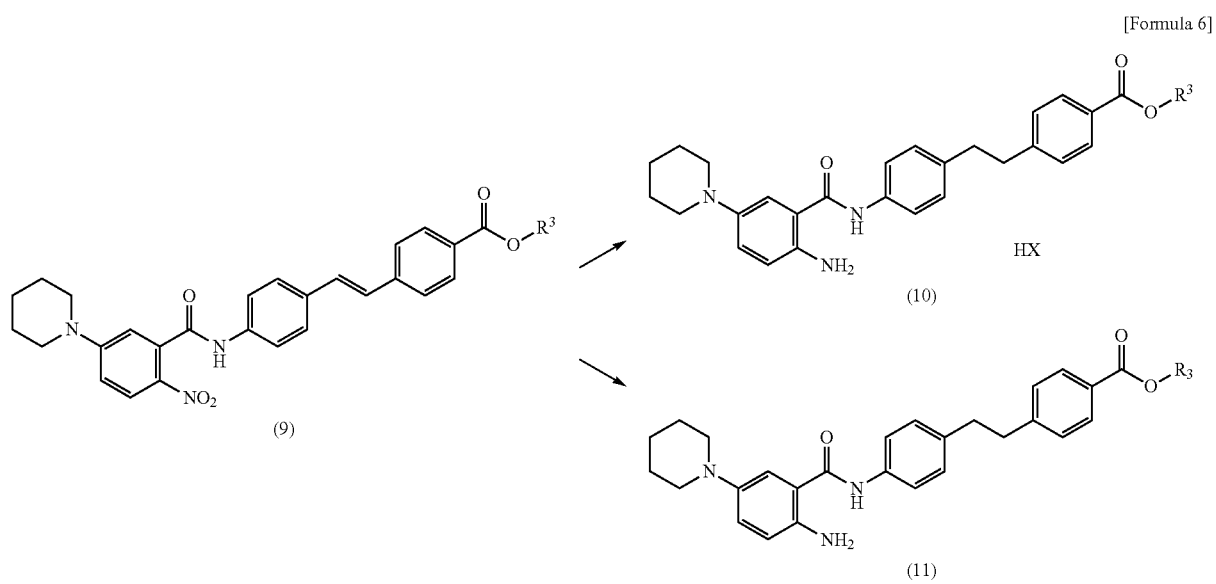

wherein $R^3$ represents a C1-C6 alkyl group and HX represents an acid.

[5]

The method according to [4] above, wherein in the step (i), the 5-chloro-2-nitrobenzoyl chloride is produced by using thionyl chloride or oxalyl chloride as a chlorinating agent and also using N,N-dimethylacetamide or N,N-dimethylformamide as a catalyst, and the base and the solvent in the condensation reaction are pyridine, triethylamine or diisopropylamine, and tetrahydrofuran or tetrahydrofuran-toluene, respectively.

[6]

The method according to [4] or [5] above, wherein in the step (ii), the solvent is N,N-dimethylacetamide or N,N-dimethylformamide.

[7]

The method for producing a compound represented by formula (10) according to any one selected from [4] to [6] above, wherein in the step (iii), the solvent is N,N-dimethylacetamide, or a mixed solvent of N,N-dimethylacetamide and ethyl acetate or methanol, and the catalyst is 5% palladium carbon, and the method further comprises a step of treating the obtained compound with hydrogen chloride.

[8]

A method for producing a compound represented by formula (6) used in the method according to any one selected from [4] to [7] above, the method comprising:

(i) a step of reacting a compound represented by formula (4) with 1-methyl-4-nitrobenzene in a solvent in the presence of C1-C6 alkyl formate and a base to produce a compound represented by formula (5):

wherein $R^3$ represents a C1-C6 alkyl group; and (ii) a step of treating the compound represented by formula (5) produced in the previous step in a solvent in the presence of a hydrogenation catalyst and a catalyst poison under a hydrogen atmosphere to produce a compound represented by formula (6):

-continued

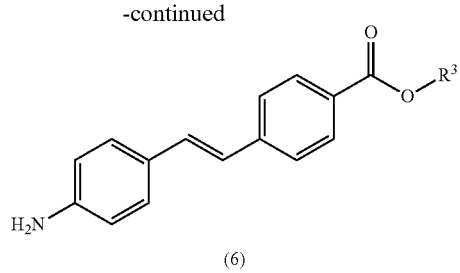

(6)

wherein R³ represents a C1-C6 alkyl group.

[9]
The method according to [8] above, wherein in the step (i), the solvent is dimethyl sulfoxide or N,N-dimethylacetamide, the C1-C6 alkyl formate is methyl formate, and the base is a solution of sodium methoxide in methanol.

[10]
The method according to [8] or [9] above, wherein in the step (ii), the solvent is N,N-dimethylacetamide or N,N-dimethylformamide, the hydrogenation catalyst is 3% platinum carbon, 0.8% platinum-0.3% molybdenum carbon, 3% platinum-0.3% iron carbon, or 1% platinum-0.1% copper carbon, and the catalyst poison is dimethyl sulfoxide.

[11]
A method for producing a compound represented by formula (3) used in the method according to any one selected from [1] to [3] above, the method comprising:
(i) a step of treating a compound represented by formula (1) in a solvent in the presence of C1-C6 alkylamine and a palladium catalyst under a hydrogen atmosphere to obtain a compound represented by formula (2); and
(ii) a step of heating and treating the compound represented by formula (2) produced in the previous step in a solvent in the presence of hydrogen chloride to obtain a compound represented by formula (3):

[Formula 9]

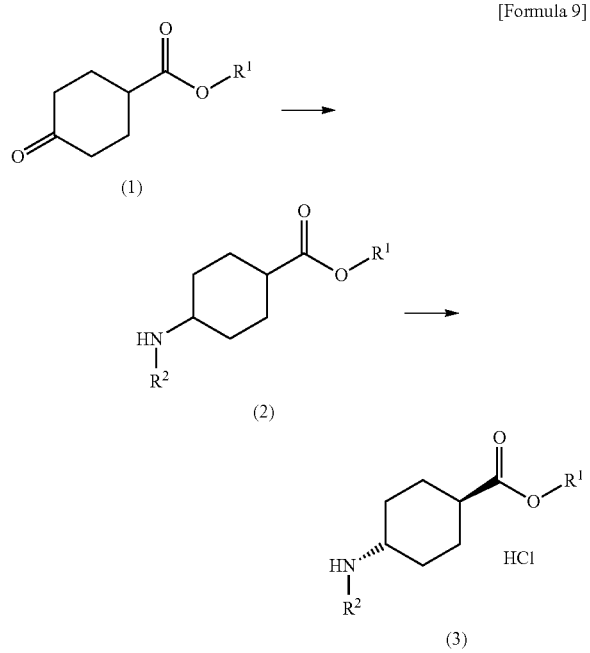

wherein R¹ represents a C1-C6 alkyl group and R² represents a C1-C6 alkyl group.

[12]
The method according to [11] above, wherein R¹ represents an ethyl group and R² represents an ethyl group.

[13]
The method according to [11] or [12] above, wherein in the step (i), the solvent is ethanol, the C1-C6 alkylamine is ethylamine, and the palladium catalyst is 5% palladium carbon.

[14]
The method according to any one selected from [11] to [13] above, wherein in the step (ii), the solvent is xylene.

[15]
The method for producing a compound represented by formula (13) or a pharmacologically acceptable salt thereof according to any one selected from [1] to [3] above, wherein a compound represented by formula (3) is produced by the method according to any one selected from [11] to [14] above, and then the compound represented by formula (3) is used.

Advantageous Effects of Invention

According to the present invention, a compound represented by formula (13) that can be industrially used as a pharmaceutical product, or a salt thereof, can be produced with a good yield and also at low cost. In addition, the present invention provides methods for producing production intermediates for the production of the compound of formula (13) with good yields at low cost.

DESCRIPTION OF EMBODIMENTS

Hereinafter, the present invention will be described in detail.

In the present description, "halogen" is a fluorine atom, a chlorine atom, a bromine atom, or an iodine atom.

In the present description, "C1-C6 alkyl group" is a linear or branched alkyl group containing 1 to 6 carbon atoms, and examples include a methyl group, an ethyl group, a propyl group, an isopropyl group, a butyl group, an isobutyl group, a sec-butyl group, a pentyl group, and a hexyl group.

In the present description, "C1-C6 alkylamine" is a linear or branched alkylamine containing 1 to 6 carbon atoms, and examples include methylamine, ethylamine, propylamine, isopropylamine, butylamine, isobutylamine, sec-butylamine, pentylamine, and hexylamine.

In the present description, examples of the acid represented by "HX" include: inorganic acids including hydrogen halides such as hydrogen fluoride, hydrogen chloride, hydrogen bromide or hydrogen iodide, nitric acid, perchloric acid, sulfuric acid, and phosphoric acid; organic acids including lower alkanesulfonic acids such as methanesulfonic acid, trifluoromethanesulfonic acid or ethanesulfonic acid, arylsulfonic acids including benzenesulfonic acid and p-toluenesulfonic acid, acetic acid, malic acid, fumaric acid, succinic acid, citric acid, ascorbic acid, tartaric acid, oxalic acid, and maleic acid; and amino acids such as glycine, lysine, arginine, ornithine, glutamic acid, or aspartic acid. Among others, hydrogen halides (in particular, hydrogen chloride) are most preferable.

In the present description, "pharmacologically acceptable salt thereof" indicates a salt that can be used as a medicament. When a compound has an acidic group or a basic group, a basic salt or an acidic salt can be formed by reacting the compound with a base or an acid. The term "pharmacologically acceptable salt thereof" indicates the thus formed salt.

Preferred examples of the pharmacologically acceptable "basic salt" of the compound include: alkali metal salts such as a sodium salt, a potassium salt, or a lithium salt; alkaline-earth metal salts such as a magnesium salt or a calcium salt; organic basic salts such as an N-methylmorpholine salt, a triethylamine salt, a tributylamine salt, a diisopropylethylamine salt, a dicyclohexylamine salt, an N-methylpiperidine salt, a pyridine salt, a 4-pyrrolidinopyridine salt, or a picoline salt; and amino acid salts such as a glycine salt, a lysine salt, an arginine salt, an ornithine salt, a glutamate, or an aspartate. Preferred examples include alkali metal salts (for example, a sodium salt).

Preferred examples of the pharmacologically acceptable "acidic salt" of the compound include: inorganic acid salts including hydrohalides such as a hydrofluoride, a hydrochloride, a hydrobromide or a hydroiodide, a nitrate, a perchlorate, a sulfate, and a phosphate; organic acid salts including lower alkanesulfonates such as methanesulfonate, trifluoromethanesulfonate or ethanesulfonate, arylsulfonates such as benzenesulfonate or p-toluenesulfonate, an acetate, a malate, a fumarate, a succinate, a citrate, an ascorbate, a tartrate, an oxalate, and a maleate; and amino acid salts such as a glycine salt, a lysine salt, an arginine salt, an ornithine salt, a glutamate, and an aspartate. Among others, hydrohalides (in particular, a hydrochloride) are most preferable.

When the compound of the present invention or a pharmacologically acceptable salt thereof is left in the air or is recrystallized, the compound or a salt thereof may absorb water and thereby contain adsorbed water, or may be converted to a hydrate. The present invention includes various types of such hydrates, solvates, and crystalline polymorphs.

The compound of the present invention, a pharmacologically acceptable salt thereof, or their solvates, may include various types of isomers including geometric isomers such as a cis isomer and a trans isomer, tautomers, and optical isomers such as a d isomer and an l isomer, depending on the types of substituent, or a combination thereof. However, the present compound includes all such isomers, steric isomers, and mixtures comprising these isomers and steric isomers at any given ratio, unless otherwise specified. A mixture of these isomers can be separated by known separation means.

Hereinafter, the present invention will be described in each production step.

[Step A] Reductive amination reaction

The present step is a step of stirring the compound represented by formula (1) according to a reductive amination reaction in a solvent in the presence of C1-C6 alkylamine and a palladium catalyst under a hydrogen atmosphere, to produce the compound represented by formula (2).

The solvent used in the present step is a linear or branched aliphatic alcohol containing 1 to 6 carbon atoms, and examples include methanol, ethanol, propanol, isopropyl alcohol, butyl alcohol, isobutyl alcohol, sec-butyl alcohol, pentyl alcohol, and hexyl alcohol. Preferably, it is appropriate to use an alcohol corresponding to $R^1$ of the present ester used as a starting material, and methanol or ethanol is preferable. The solvent is used in an amount of 0.1 to 10 times by weight, and preferably 4 to 6 times by weight.

The C1-C6 alkylamine used in the present step is a linear or branched alkylamine, and examples include methylamine, ethylamine, propylamine, isopropylamine, butylamine, isobutylamine, sec-butylamine, pentylamine, and hexylamine. Among others, methylamine or ethylamine is preferable. The C1-C6 alkylamine is used in an amount of 1.0 to 4.0 equivalents, and preferably 1.5 to 2.5 equivalents.

Examples of the catalyst used in the present step include palladium catalysts such as palladium-carbon, palladium black, palladium hydroxide or palladium-barium sulfate, platinum catalysts such as platinum oxide or platinum black, rhodium catalysts such as rhodium-aluminum oxide or triphenylphosphine-rhodium chloride, and nickels such as Raney nickel. Among others, palladium carbon is preferable, and 5% palladium carbon (PE type manufactured by N. E. Chem cat, or M type manufactured by Kawaken Fine Chemicals Co., Ltd.) is more preferable. The palladium catalyst is used, on a dry basis, in an amount of 0.03 to 0.8 times by weight, and preferably 0.04 to 0.2 times by weight.

The pressure of hydrogen in the present step is, for example, 0.0 to 1.0 MPaG, and preferably 0.1 to 0.5 MPaG.

The reaction temperature in the present step is 0° C. to 100° C., preferably 20° C. to 60° C., and more preferably 30° C. to 50° C.

The reaction time in the present step is 1 to 14 hours, and preferably 2 to 5 hours.

[Step B] Separation of trans Isomer and cis isomer

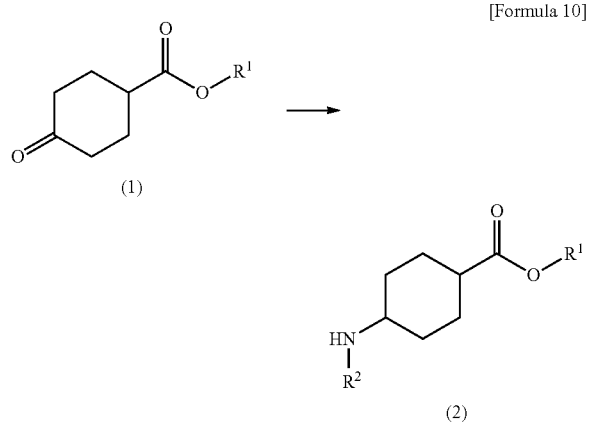

[Formula 10]

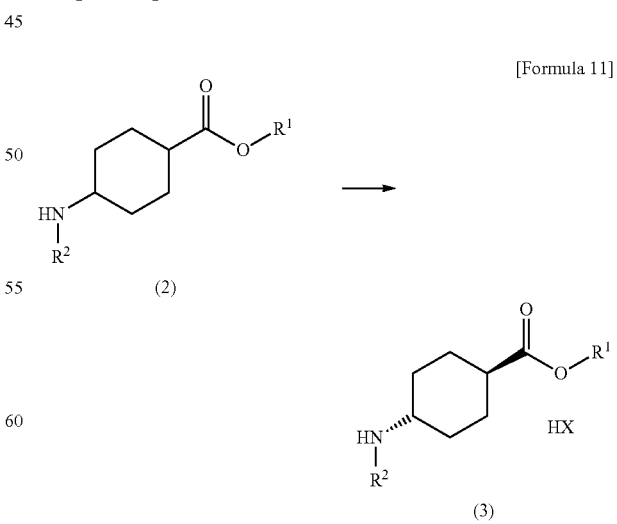

[Formula 11]

wherein $R^1$ represents a C1-C6 alkyl group, and $R^2$ represents a C1-C6 alkyl group.

wherein $R^1$ and $R^2$ are as defined above, and HX represents an acid.

The present step is a step of heating and stirring the compound represented by formula (2) in a solvent in the presence of an acid, to produce the compound represented by formula (3).

In the present reaction, the reaction rate can be accelerated by adding a suitable amount of acid, so that workload can be reduced. In addition, by adding a suitable amount of acid, the hydrochloride (3) of the trans isomer can be isolated without removing lactam generated from the cis isomer by crystallization or distillation, so that workload can be further reduced.

When the trans isomer (3) is separated in the form of a hydrochloride, if an excess amount of hydrochloric acid is present, lactam contamination occurs and, as a result, the crystals become deliquescent. Accordingly, it is important to regulate the amount of acid.

Moreover, although the hydrochloride (3) of a trans isomer is a salt, it is easily dissolved in a solvent such as acetonitrile. Accordingly, in order to progress the present step, it is also important to select a solvent to be used in crystallization.

Examples of the solvent used in the reaction in the present step include solvents such as mesitylene, xylene, toluene, ethyl acetate or acetic acid butyl ester, and several solvents may be mixed. Among these solvents, mesitylene, xylene and toluene are preferable, and xylene is more preferable. Such xylene may be in the form of a mixture with a regioisomer or ethylbenzene. With regard to the amount of such a solvent used, xylene is used in an amount of 5 to 15 times, and preferably 8 to 10 times, based on the weight of the trans isomer of (2).

Examples of the acid used in the reaction in the present step include hydrogen chloride, hydrogen bromide, hydrogen iodide, sulfuric acid, phosphoric acid, methanesulfonic acid, p-toluenesulfonic acid, and camphorsulfonic acid. Among these acids, hydrogen chloride, hydrogen bromide and hydrogen iodide are preferable, and hydrogen chloride is more preferable. Hydrogen chloride, which is dissolved in a non-aqueous solvent such as an ethyl acetate solution or a dioxane solution, may also be used. The acid is used in an amount of 0.6 to 1.2 equivalents, and preferably 0.7 to 0.8 equivalents, based on the amount of the trans isomer of (2).

As a solvent used in the crystallization operation in the present step, the solvent used during the reaction may be used as is. Preferably, the solvent is a mixed solvent of xylene and ethyl acetate, and xylene may also be a mixture with a regioisomer. With regard to the amount of the solvent used, xylene is used in an amount of 5 to 15 times, and preferably 8 to 10 times, based on the weight of the trans isomer of (2). In addition, ethyl acetate is used in an amount of 0 to 11.5 times, and preferably 5.0 to 6.5 times, based on the weight of the trans isomer of (2).

Examples of the acid used in the crystallization operation in the present step include hydrogen chloride, hydrogen bromide, hydrogen iodide, sulfuric acid, phosphoric acid, methanesulfonic acid, p-toluenesulfonic acid, and camphorsulfonic acid. Among these acids, hydrogen chloride, hydrogen bromide and hydrogen iodide are preferable, and hydrogen chloride is more preferable. Hydrogen chloride, which is dissolved in a non-aqueous solvent such as an ethyl acetate solution or a dioxane solution, may also be used. With regard to the total amount of the acid used, the acid is used in an amount of 1.0 to 1.2 equivalents, and preferably 1.0 to 1.1 equivalents, based on the amount of the trans isomer of (2).

The reaction temperature in the present step is 100° C. to 150° C., and preferably 120° C. to 140° C.

The reaction time in the present step is 1 to 24 hours, and preferably 6 to 12 hours.

[Step C]

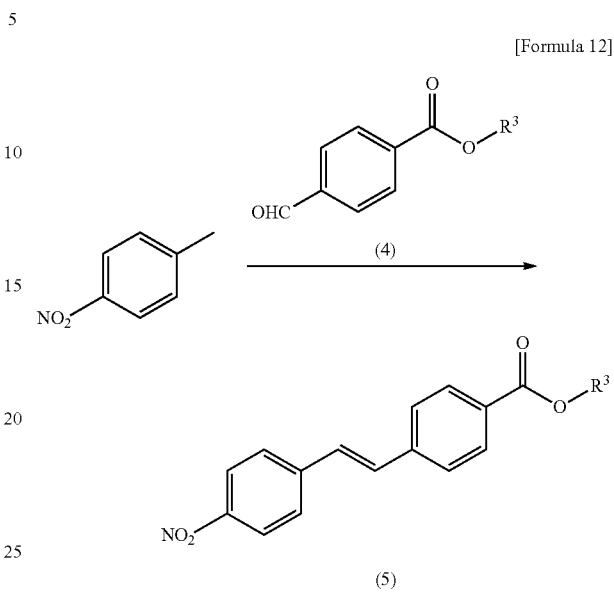

[Formula 12]

wherein $R^3$ represents a C1-C6 alkyl group.

The present step is a method for producing the compound represented by formula (5), which comprises stirring the compound represented by formula (4) and an inexpensive starting material, 1-methyl-4-nitrobenzene, in a solvent, in the presence of C1-C6 alkyl formate and a base. The present step is characterized in that it comprises reacting a compound having both an ester and an aldehyde, such as the compound represented by formula (4), with 1-methyl-4-nitrobenzene.

In the present step, 1-methyl-4-nitrobenzene is used in an amount of 0.5 to 3.0 equivalents, and preferably 0.8 to 1.2 equivalents.

Examples of the solvent used in the present step include dimethyl sulfoxide, N,N-dimethylacetamide, N,N-dimethylformamide, 1,3-dimethyl-2-imidazolidinone, N-methylpyrrolidone, sulfolane and N,N'-dimethylpropyleneurea, and among these solvents, dimethyl sulfoxide and N,N-dimethylacetamide are preferable. The solvent is used in an amount of 2 to 50 times by weight, preferably 5 to 30 times by weight, and more preferably 8 to 20 times by weight.

The C1-C6 alkyl formate used in the present step is an ester formed from formic acid and C1-C6 alkyl alcohol, and preferably, it is appropriate to use alcohol corresponding to $R^3$ of the present ester used as a starting material. Examples include methyl formate, ethyl formate, propyl formate, and isopropyl formate, and among others, methyl formate is preferable. The C1-C6 alkyl formate is used in an amount of 1 to 10 equivalents, and preferably 1.5 to 4 equivalents. In the present step, it is important to add C1-C6 alkyl formate because the reaction can be carried out with a high yield by the addition thereof.

As a base used in the present step, it is appropriate to use the alcoholate of the alcohol corresponding to $R^3$ of the present ester used as a starting material. Preferred examples of the base used herein include alkali metal salts such as sodium methoxide, potassium methoxide or lithium methoxide. More preferably, the base is sodium methoxide, and a solution of sodium methoxide in methanol may be preferable. The base is used in an amount of 0.5 to 3 equivalents, and preferably 1.2 to 2.5 equivalents.

The reaction temperature in the present step is 0° C. to 50° C., and preferably 10° C. to 30° C.

The reaction time in the present step is 0.5 to 20 hours, and preferably 0.5 to 5 hours.

[Step D]

[Formula 13]

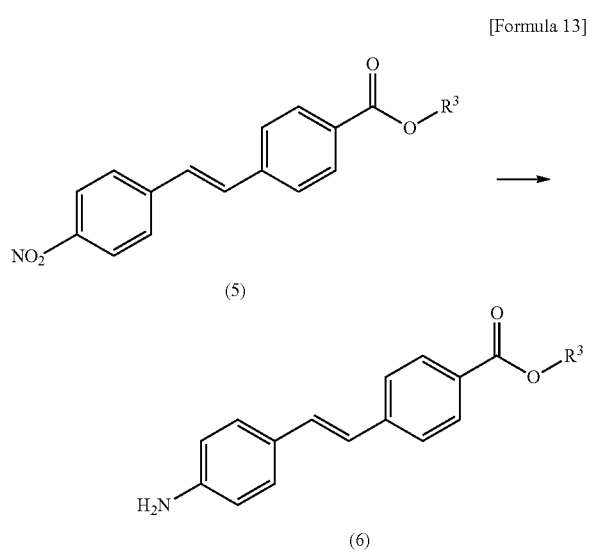

(6)

wherein $R^3$ represents a C1-C6 alkyl group.

The present step is a step of stirring the compound represented by formula (5) in a solvent in the presence of a hydrogenation catalyst and a catalyst poison under a hydrogen atmosphere, to produce the compound represented by formula (6). The present step is characterized in that only the nitro group can be selectively hydrogenated in the presence of a double bond.

Examples of the solvent used in the present step include N,N-dimethylacetamide, N,N-dimethylformamide, 1,3-dimethyl-2-imidazolidinone, N-methylpyrrolidone and N,N'-dimethylpropyleneurea, and among these solvents, N,N-dimethylacetamide and N,N-dimethylformamide are preferable. The solvent is used in an amount of 5 to 30 times by weight, and preferably 6 to 15 times by weight.

An example of the hydrogenation catalyst used in the present step is platinum carbon, and the platinum carbon may comprise iron, copper, or molybdenum. The hydrogenation catalyst used may be preferably 0.5% to 5% platinum carbon, and more preferably 0.8% to 3% platinum carbon, and further preferably 0.8% platinum-0.3% molybdenum carbon (manufactured by BASF), 3% platinum-0.3% iron carbon (manufactured by Evonik), or 1% platinum-0.1% copper carbon (manufactured by Evonik). The hydrogenation catalyst is used, on a dry basis, in an amount of 0.005 to 0.5 times by weight, and preferably 0.02 to 0.3 times by weight.

The catalyst poison used in the present step is dimethyl sulfoxide, and the catalyst poison is used in an amount of 0.02 to 0.5 times by weight, and preferably 0.03 to 0.2 times by weight.

The reaction pressure in the present step is 0 to 1.0 MPaG, and preferably 0 to 0.5 MPaG. It is also possible to use a hydrogen source such as ammonium formate.

The reaction temperature in the present step is 0° C. to 150° C., preferably 20° C. to 100° C., and more preferably 30° C. to 60° C.

The reaction time in the present step is 0.5 to 30 hours, and preferably 1 to 6 hours.

[Step E]

[Formula 14]

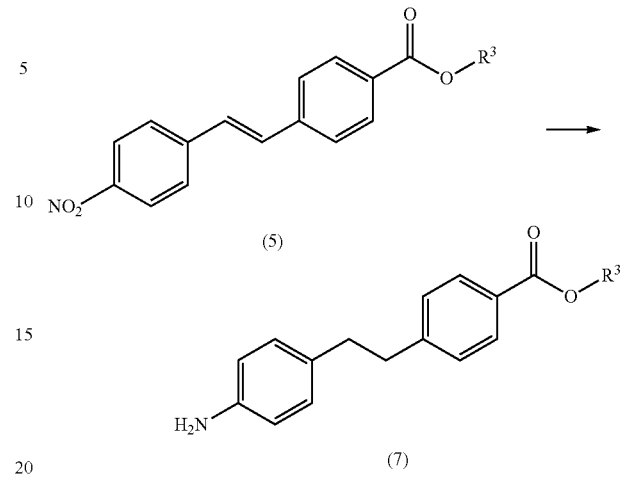

wherein $R^3$ represents a C1-C6 alkyl group.

The present step is a step of stirring the compound represented by formula (5) according to a reduction reaction in a solvent in the presence of a palladium catalyst under a hydrogen atmosphere, to produce the compound represented by formula (7).

Examples of the solvent used in the present step include N,N-dimethylacetamide, N,N-dimethylformamide, 1,3-dimethyl-2-imidazolidinone, N-methylpyrrolidone and N,N'-dimethylpropyleneurea, and among these solvents, N,N-dimethylacetamide and N,N-dimethylformamide are preferable. The solvent is used in an amount of 3 to 30 times by weight, and preferably 5 to 15 times by weight.

Examples of the catalyst used in the present step include palladium catalysts such as palladium-carbon, palladium black, palladium hydroxide or palladium-barium sulfate, platinum catalysts such as platinum oxide or platinum black, rhodium catalysts such as rhodium-aluminum oxide or triphenylphosphine-rhodium chloride, and nickel catalysts such as Raney nickel. Among others, palladium carbon is preferable, and 5% palladium carbon is more preferable. The palladium catalyst is used in an amount of 0.03 to 0.8 times by weight, and preferably 0.04 to 0.2 times by weight.

In the present step, the reaction is carried out under a hydrogen atmosphere. The reaction pressure is, for example, 0.0 to 1.0 MPaG, and preferably 0.1 to 0.5 MPaG.

The reaction temperature in the present step is 0° C. to 150° C., preferably 20° C. to 100° C., and more preferably 30° C. to 50° C.

The reaction time in the present step is 1 to 14 hours, and preferably 2 to 5 hours.

[Step F]

[Formula 15]

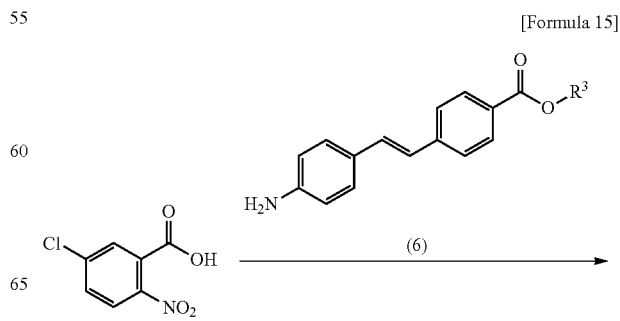

-continued

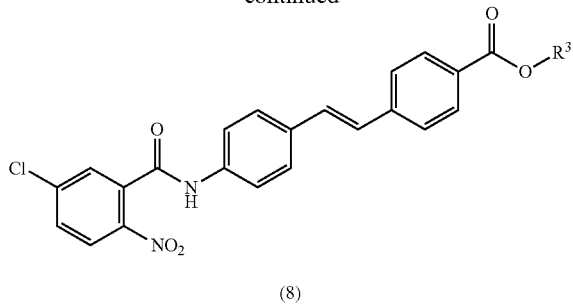

(8)

wherein R³ represents a C1-C6 alkyl group.

The present step is a step of stirring the compound represented by formula (6) in a solvent according to a condensation reaction with 5-chloro-2-nitrobenzoyl chloride obtained from 5-chloro-2-nitrobenzoic acid used as an inexpensive starting material, to produce the compound represented by formula (8). The compound represented by formula (8) can also be used in the subsequent step without being isolated.

5-Chloro-2-nitrobenzoyl chloride is synthesized by stirring 5-chloro-2-nitrobenzoic acid and a chlorinating agent in a solvent in the presence of a catalyst.

5-Chloro-2-nitrobenzoic acid is used in the step of synthesizing acid chloride in an amount of 0.9 to 2.0 equivalents, and preferably 1.0 to 1.2 equivalents, based on the amount of the compound of formula (6) used in the condensation step.

The chlorinating agent used in the step of synthesizing the acid chloride is thionyl chloride, oxalyl chloride or phosphoryl chloride, and it is preferably thionyl chloride or oxalyl chloride. The chlorinating agent is used in an amount of 1.0 to 10 equivalents, and preferably 1.0 to 2.0 equivalents.

The catalyst used in the step of synthesizing the acid chloride is N,N-dimethylacetamide or N,N-dimethylformamide, and the catalyst is used in an amount of 0.001 time to 0.1 time by weight, and preferably 0.005 times to 0.03 times by weight.

The solvent used in the step of synthesizing the acid chloride is not particularly limited, as long as it is a solvent that does not inhibit the reaction. Examples of the solvent include aromatic hydrocarbons such as toluene, esters such as ethyl acetate, ethers such as tetrahydrofuran, aliphatic hydrocarbons such as cyclohexane, and nitriles such as acetonitrile. Among these solvents, toluene, ethyl acetate, tetrahydrofuran and acetonitrile are preferable, and toluene and ethyl acetate are more preferable. The solvent is used in an amount of 3 to 10 times by weight.

The reaction temperature applied in the step of synthesizing the acid chloride is 30° C. to 110° C., and preferably 50° C. to 70° C.

The reaction time applied in the step of synthesizing the acid chloride is 0.5 to 24 hours, and preferably 1 to 5 hours.

Examples of the base used in the condensation step include triethylamine, diethylisopropylamine, diisopropylethylamine, N-methylmorpholine, dimethylbenzylamine, 1,8-diazabicyclo[5.4.0]undec-7-ene, pyridine and 2,6-lutidine. Among these bases, pyridine, triethylamine and diisopropylamine are preferable. The base is used in an amount of 1.1 to 10 equivalents, and preferably 1.5 to 3.0 equivalents.

The solvent used in the condensation step is not particularly limited, as long as it is a solvent that does not inhibit the reaction. Examples of the solvent include aromatic hydrocarbons such as toluene, esters such as ethyl acetate, ethers such as tetrahydrofuran, aliphatic hydrocarbons such as cyclohexane, and nitriles such as acetonitrile. Among these solvents, tetrahydrofuran, acetonitrile, ethyl acetate, toluene and a mixed solvent thereof are preferable, and tetrahydrofuran and tetrahydrofuran-toluene are more preferable.

The reaction temperature applied in the condensation step is 0° C. to 100° C., and preferably 10° C. to 60° C.

The reaction time applied in the condensation step is 0.5 to 24 hours, and preferably 1 to 5 hours.

[Step G]

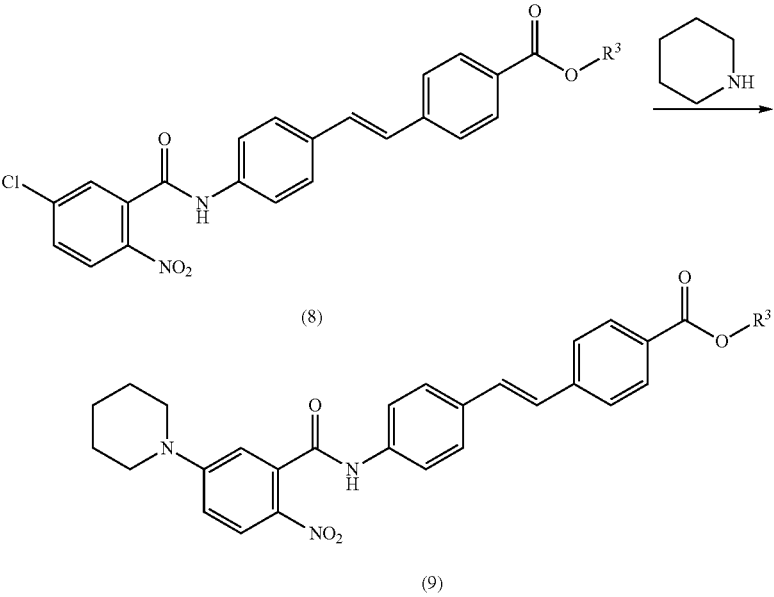

wherein R³ represents a C1-C6 alkyl group.

The present step is a step of reacting the compound represented by formula (8) with piperidine and stirring them in a solvent to produce the compound represented by formula (9).

Piperidine is used in the present step in an amount of 1 to 10 equivalents, and preferably 3 to 5 equivalents.

The reaction temperature in the present step is 80° C. to 150° C., and preferably 90° C. to 110° C.

Examples of the solvent used in the present step include N,N-dimethylacetamide, N,N-dimethylformamide, 1,3-dimethyl-2-imidazolidinone, N-methylpyrrolidone, N,N'-dimethylpropyleneurea and dimethyl sulfoxide, and among these solvents, N,N-dimethylacetamide and N,N-dimethylformamide are preferable. The solvent is used in an amount of 3 to 30 times by weight, preferably 5 to 20 times by weight, and more preferably 8 to 15 times by weight.

The reaction time in the present step is 1 to 24 hours, and preferably 2 to 6 hours.

[Step H]

mula (11); or a step of stirring the compound represented by formula (9) according to a reduction reaction in a solvent in the presence of a catalyst under a hydrogen atmosphere, and then treating it with a suitable acid, to produce the compound represented by formula (10).

Examples of the solvent used in the present step include polar solvents that are used alone, such as N,N-dimethylacetamide, N,N-dimethylformamide, 1,3-dimethyl-2-imidazolidinone, N-methylpyrrolidone and N,N'-dimethylpropyleneurea, and mixed solvents obtained by mixing these polar solvents with ethyl acetate or methanol. Among these solvents, polar solvents used alone, such as N,N-dimethylacetamide or N,N-dimethylformamide, and mixed solvents obtained by mixing these polar solvents with ethyl acetate or methanol, are preferable, and N,N-dimethylacetamide alone and a mixed solvent of the polar solvent with ethyl acetate or methanol are more preferable. With regard to the mixing ratio, ethyl acetate or methanol is used in an amount of 9 times or less, preferably 1 to 5 times, and more preferably 1 to 2 times, based on the weight of the polar solvent defined

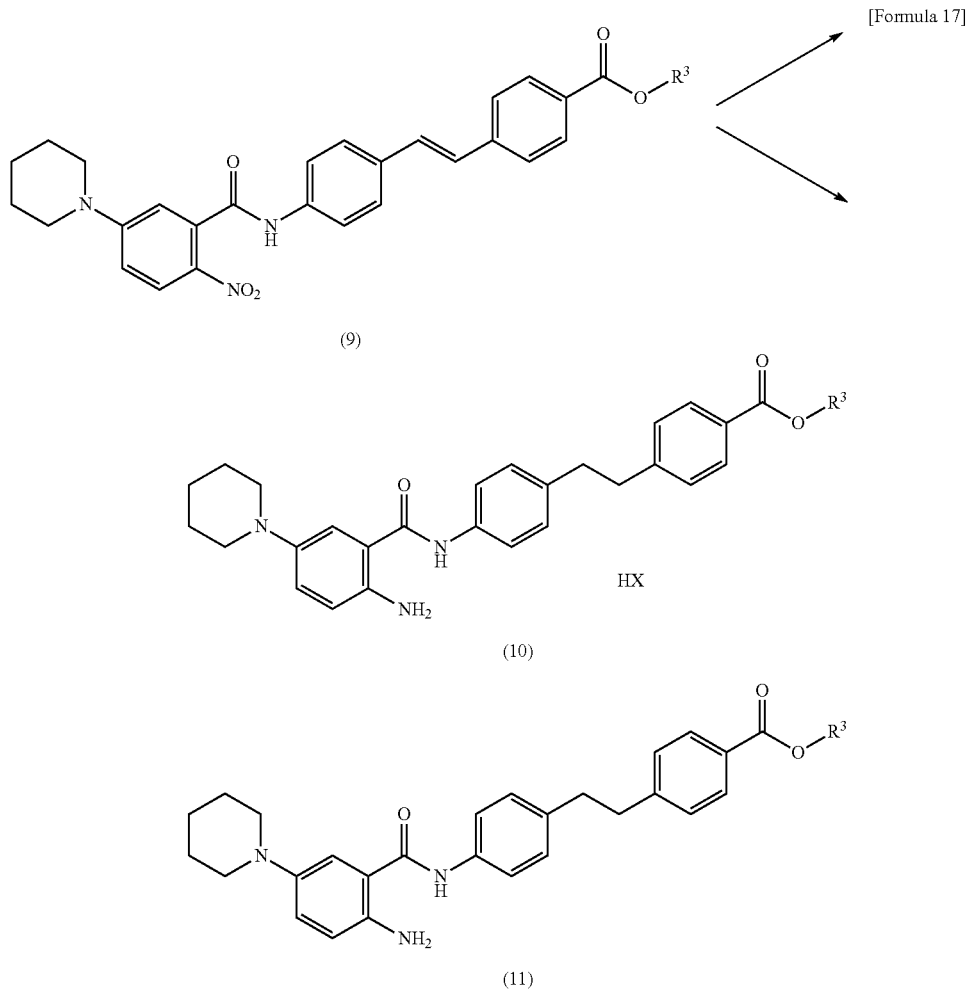

[Formula 17]

(9)

(10)

(11)

wherein $R^3$ represents a C1-C6 alkyl group, and HX represents an acid.

The present step is a step of stirring the compound represented by formula (9) according to a reduction reaction in a solvent in the presence of a catalyst under a hydrogen atmosphere, to produce the compound represented by formula (11); or a step of stirring the compound represented by formula (9) according to a reduction reaction in a solvent in the presence of a catalyst under a hydrogen atmosphere, and then treating it with a suitable acid, to produce the compound represented by formula (10).

as 1. Moreover, the solvent is used in an amount of 3 to 30 times by weight, preferably 5 to 15 times by weight, and more preferably 10 to 15 times by weight.

Examples of the catalyst used in the present step include palladium catalysts such as palladium-carbon, palladium black, palladium hydroxide or palladium-barium sulfate, platinum catalysts such as platinum oxide or platinum black, rhodium catalysts such as rhodium-aluminum oxide or triphenylphosphine-rhodium chloride, and nickels such as Raney nickel. Among others, palladium carbon is preferable, and 5% palladium carbon is more preferable. The palladium catalyst is used in an amount of 0.03 to 0.8 times by weight, and preferably 0.05 to 0.2 times by weight.

The present step is carried out under a hydrogen atmosphere. The reaction pressure is, for example, 0.0 to 1.0 MPaG, and preferably 0.1 to 0.5 MPaG.

The reaction temperature in the present step is 0° C. to 150° C., preferably 20° C. to 100° C., and more preferably 40° C. to 70° C.

The reaction time in the present step is 1 to 24 hours, and preferably 1 to 5 hours.

After the removal of the catalyst, a suitable treatment is carried out as a post-treatment of the present step, so that a salt with an acid, or a free amine can be obtained in the form of crystals.

Examples of the acid used in the post-treatment of the present step include hydrogen chloride, hydrogen bromide, hydrogen iodide, sulfuric acid, phosphoric acid, methanesulfonic acid, p-toluenesulfonic acid, and camphorsulfonic acid. Among these acids, hydrogen chloride, hydrogen bromide and hydrogen iodide are preferable, and hydrogen chloride is more preferable. Hydrogen chloride, which is dissolved in a non-aqueous solvent such as an ethyl acetate solution or a dioxane solution, may also be used. The acid is used in an amount of 0.8 to 2.0 equivalents, and preferably 1 to 1.2 equivalents.

[Step I]

wherein $R^1$ represents a C1-C6 alkyl group, $R^2$ represents a C1-C6 alkyl group, $R^3$ represents a C1-C6 alkyl group, and HX represents an acid.

The present step is a step of stirring the compound represented by formula (10) and 3-(chlorosulfonyl)benzoyl chloride, which has been prepared separately, in a solvent, and then stirring an intermediate obtained by an amidation reaction (wherein the intermediate can also be isolated as a hydrochloride) and the compound represented by formula (3) in a solvent to carry out a sulfonamidation reaction, so as to produce the compound represented by formula (12).

It may be possible to use the compound represented by the formula (10) as is, or to use the compound represented by formula (11), or as necessary, to use the compound represented by formula (11) in the form of a solution.

3-(Chlorosulfonyl)benzoyl chloride is used in the amidation reaction in an amount of 0.8 to 1.5 equivalents, and preferably 1.0 to 1.2 equivalents.

Examples of the solvent used in the amidation reaction include N,N-dimethylacetamide, N,N-dimethylformamide, 1,3-dimethyl-2-imidazolidinone, N-methylpyrrolidone, N,N'-dimethylpropyleneurea, dimethyl sulfoxide, acetonitrile and acetonitrile-tetrahydrofuran, and among these solvents, N,N-dimethylacetamide, acetonitrile and acetonitrile-tetrahydrofuran are preferable. The solvent is used in an amount of 5 to 30 times by weight, preferably 8 to 20 times by weight, and more preferably 15 to 18 times by weight.

The reaction temperature applied in the amidation reaction is 0° C. to 60° C., preferably 10° C. to 40° C., and more preferably 10° C. to 30° C.

The reaction time applied in the amidation reaction is 0.5 to 24 hours, and preferably 1 to 5 hours.

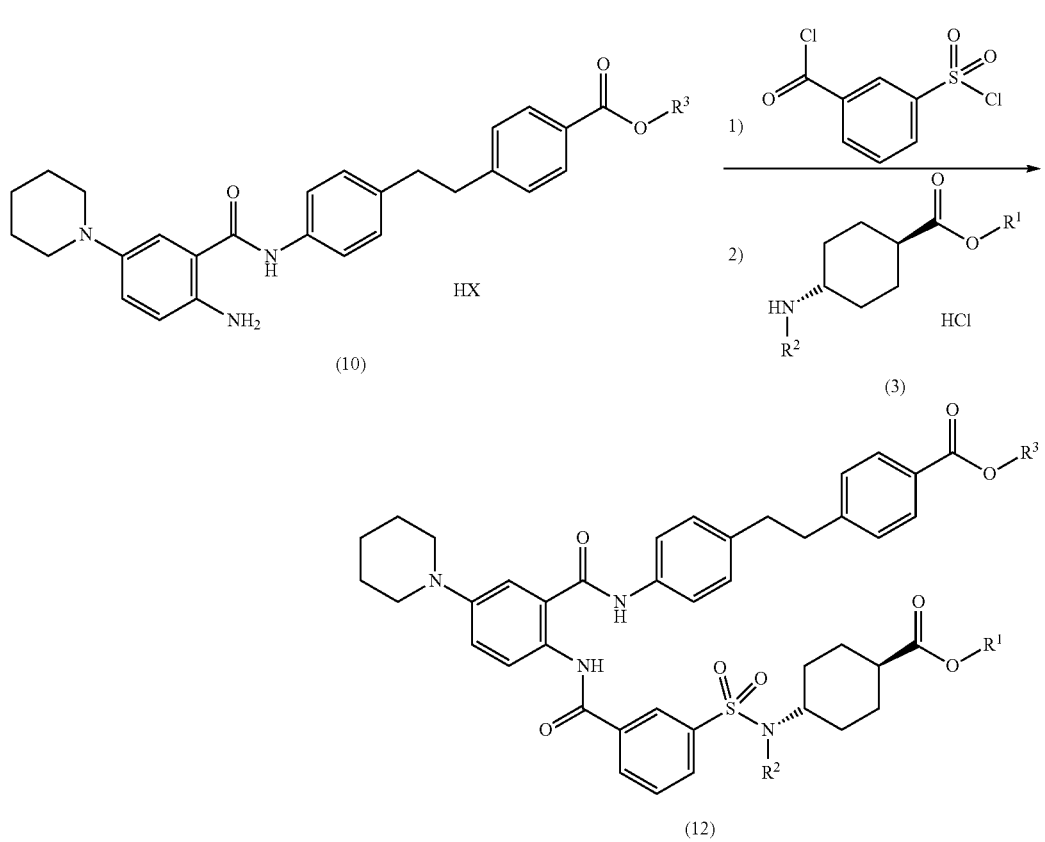

[Formula 18]

The compound represented by formula (3) is used in the sulfonamidation reaction in an amount of 1.0 to 3.0 equivalents, and preferably 1.1 to 2.0 equivalents.

Examples of the solvent used in the sulfonamidation reaction include N,N-dimethylacetamide, N,N-dimethylformamide, 1,3-dimethyl-2-imidazolidinone, N-methylpyrrolidone, N,N'-dimethylpropyleneurea, dimethyl sulfoxide, tetrahydrofuran and acetonitrile-tetrahydrofuran, and among these solvents, N,N-dimethylacetamide, tetrahydrofuran and acetonitrile-tetrahydrofuran are preferable. The solvent is used in an amount of 3 to 30 times by weight, preferably 8 to 20 times by weight, and more preferably 15 to 18 times by weight.

The amount of trimethylsilyl chloride used in the sulfonamidation reaction is set at 0.5 to 1.2 equivalents, and preferably 0.7 to 1.0 equivalents. By using trimethylsilyl chloride, the yield can be improved.

Examples of the base used in the sulfonamidation reaction include triethylamine, diethylisopropylamine, diisopropylethylamine, tributylamine, N-methylmorpholine, dimethylbenzylamine, 1,8-diazabicyclo[5.4.0]undec-7-ene, pyridine, 2,6-lutidine, cesium carbonate and potassium carbonate, and among these bases, triethylamine, diethylisopropylamine, N-methylmorpholine, dimethylbenzylamine and cesium carbonate are preferable. The base is used in an amount of 3 to 10 equivalents, and preferably 4 to 7 equivalents.

The reaction temperature applied in the sulfonamidation reaction is 0° C. to 30° C., and preferably 5° C. to 20° C.

The reaction time applied in the sulfonamidation reaction is 0.5 to 24 hours, and preferably 1 to 6 hours.

[Step J]

wherein $R^1$ represents a C1-C6 alkyl group, $R^2$ represents a C1-C6 alkyl group, and $R^3$ represents a C1-C6 alkyl group.

The present step is a step of stirring the compound represented by formula (12) in the presence of aqueous alkali in a solvent to carry out a hydrolysis reaction, so as to produce the compound represented by formula (13).

Examples of the aqueous alkali used in the present step include an aqueous sodium hydroxide solution, an aqueous potassium hydroxide solution, an aqueous lithium hydroxide solution, and an aqueous barium hydroxide solution. Among these aqueous solutions, an aqueous sodium hydroxide solution is preferable. This aqueous solution is used in an amount of 2.1 to 10 equivalents, and preferably 3 to 5 equivalents, and the concentration of the aqueous solution is 1 to 10 N, and preferably 3 to 5 N.

Examples of the solvent used in the present step include N,N-dimethylacetamide, N,N-dimethylformamide, 1,3-dimethyl-2-imidazolidinone, N-methylpyrrolidone, N,N'-dimethylpropyleneurea, dimethyl sulfoxide, methanol, ethanol, 1-propanol, 2-propanol, 2-methyl-2-propanol, tetrahydrofuran, 1,4-dioxane and acetonitrile, each of which is used alone, or as a mixed solvent thereof. Preferred examples of the solvent include N,N-dimethylacetamide, N,N-dimethylformamide, methanol, methanol-tetrahydrofuran and methanol-acetonitrile, and among others, N,N-dimethylacetamide, methanol-tetrahydrofuran (volume ratio: 1:0.5-2) and methanol-acetonitrile (volume ratio: 1:0.5-2) are more preferable. The solvent is used in an amount of 3 to 30 times by weight, preferably 5 to 15 times by weight, and more preferably 8 to 15 times by weight.

[Formula 19]

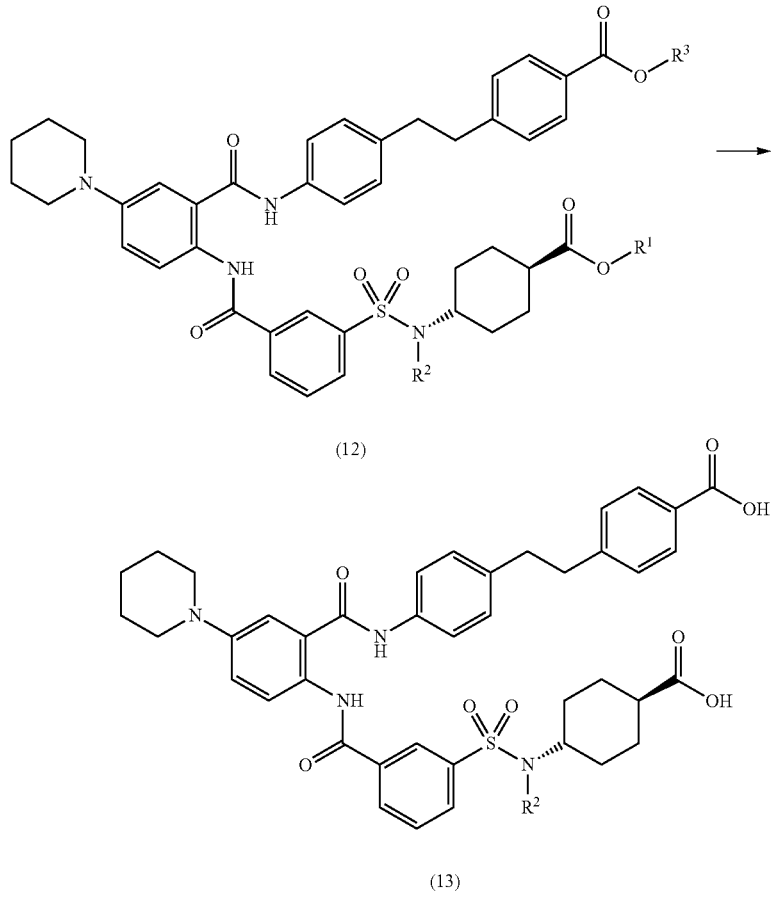

The reaction temperature is 0° C. to 100° C., preferably 20° C. to 60° C., and more preferably 40° C. to 60° C.

The reaction time is 2 to 24 hours, and preferably 3 to 8 hours.

Individual compounds used in each step are each isolated and purified in the form of a free form or a salt thereof. Such isolation and/or purification is carried out by operations conducted in ordinary organic synthetic chemistry, such as extraction, fractional crystallization, and various types of chromatography.

EXAMPLES

Hereinafter, the present invention will be described in more detail in the following Examples. However, these Examples are not intended to limit the scope of the present invention.

As an internal standard substance in the nuclear magnetic resonance spectra (NMR), tetramethylsilane was used. The abbreviations indicating multiplicity are as follows: s=singlet, d=doublet, t=triplet, q=quartet, m=multiplet, and br s=broad singlet.

Example 1

Methyl 4-[(E)-2-(4-nitrophenyl)ethenyl]benzoate (5-m)

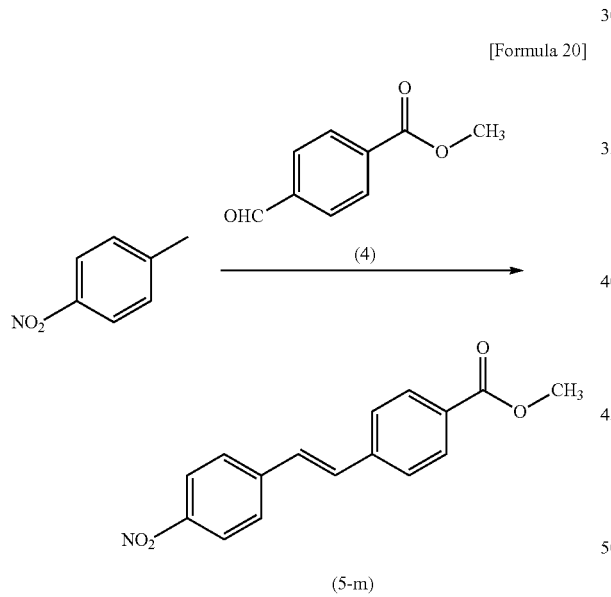

[Formula 20]

(5-m)

A solution of 15.00 Kg (0.091 kmol) of methyl 4-formylbenzoate and 12.53 Kg (1.0 equivalent) of 1-methyl-4-nitrobenzene in N,N-dimethylacetamide (56.4 L) was deaerated under reduced pressure, and then 11.00 Kg (2.0 equivalents) of methyl formate was added to the solution. Under a nitrogen atmosphere, this solution was added dropwise to a solution of 26.44 Kg (1.5 equivalents) of a 28% sodium methoxide in methanol solution in N,N-dimethylacetamide (141.0 Kg), which had been deaerated under reduced pressure, at an internal temperature of 14° C. to 23° C. over about 1 hour, followed by fully washing with 14.1 Kg of N,N-dimethylacetamide, which had been deaerated under reduced pressure. The resulting mixture was stirred at the same temperature for 2.25 hours, and then 8.30 Kg (1.5 equivalents) of acetic acid, which had been deaerated under reduced pressure, was added dropwise thereto at the same temperature over 10 minutes. 75 L of water, which had been deaerated under reduced pressure, was added dropwise thereto at 21° C. to 25° C. over about 0.5 hours. The resulting mixture was stirred at the same temperature overnight, and then the precipitated crystals were filtered. The crystals were successively washed with 81.5 L of a mixed solvent of deaerated N,N-dimethylacetamide and water (3:1), and then with 81.5 L of water. The obtained wet crystals were dried at an external temperature of 60° C. under reduced pressure to obtain 21.44 Kg of methyl 4-[(E)-2-(4-nitrophenyl)ethenyl]benzoate (yield: 82.8%). Melting point: 195.4° C. $^1$H-NMR (500 MHz, DMSO-$d_6$) δ: 3.865 (3H, s), 7.579 (1H, d, J=14.0 Hz), 7.621 (1H, d, J=14.0 Hz), 7.817 (2H, dd, J=2.0, 6.5 Hz), 7.920 (2H, ddd, J=2.5, 4.5, 9.5 Hz), 7.995 (2H, ddd, J=2.5, 4.5, 9.5 Hz).

Example 2

Methyl 4-[(E)-2-(4-nitrophenyl)ethenyl]benzoate (5-m)

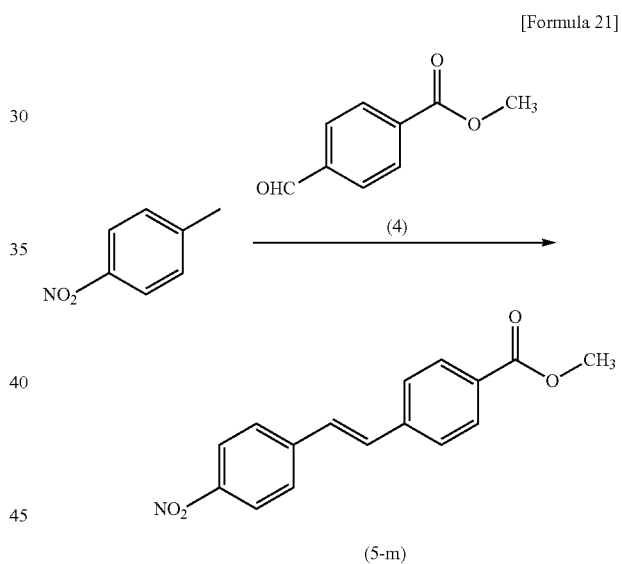

[Formula 21]

(5-m)

4.17 g (30.45 mmol) of 1-Methyl-4-nitrobenzene, 5.5 g (1.1 equivalents) of methyl 4-formylbenzoate, and 3.73 mL (2.0 equivalents) of methyl formate were dissolved in 50 mL of N,N-dimethylacetamide. To this solution, a solution prepared by diluting 8.81 g (1.5 equivalents) of a 28% sodium methoxide in methanol solution with 20 mL of N,N-dimethylacetamide was added dropwise at an internal temperature of 20° C. to 25° C. over about 1 hour, followed by fully washing with 5 mL of N,N-dimethylacetamide. The resulting mixture was stirred at the same temperature for 1 hour, and then 2.61 mL (1.5 equivalents) of acetic acid was added dropwise thereto over 30 minutes. To this reaction solution, a solution of 0.5 g of sodium hydrogen sulfite in water (25 mL) was added dropwise at 20° C. to 25° C. over about 1 hour. The resulting mixture was stirred at the same temperature for 1.5 hours. Thereafter, the precipitated crystals were filtered and were successively washed with 35 mL of a mixed solution of N,N-dimethylacetamide and water (3:1) and then with 25 mL of water. The obtained wet crystals were dried at an external temperature of 60° C. under reduced pressure to obtain 7.68 g of the title compound (yield: 89.0%).

Example 3

Methyl 4-[(E)-2-(4-aminophenyl)ethenyl]benzoate (6-m)

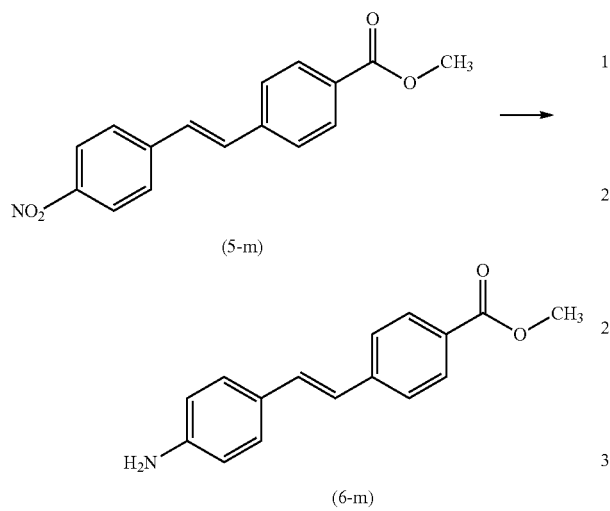

Under a nitrogen atmosphere, 10.54 Kg of the methyl 4-[(E)-2-(4-nitrophenyl)ethenyl]benzoate produced in Example 1 (0.037 kmol basis), 69.4 Kg of N,N-dimethylacetamide, 0.57 Kg of 3% platinum-0.3% iron carbon (manufactured by Evonik, 58.9% wet product), and 0.58 Kg of dimethyl sulfoxide were added. After replacement by a hydrogen atmosphere, the resulting mixture was stirred under a hydrogen pressure of 0.5 MPaG at 12° C. to 58° C. for about 4.5 hours.

After replacement by a nitrogen atmosphere, the mixture was cooled to about 25° C. and allowed to stand overnight. The mixture was heated to an internal temperature of 55° C., and then the catalyst was filtered. The catalyst was washed with 29.7 Kg of N,N-dimethylacetamide, and then the filtrates were combined. The obtained solution was heated to an internal temperature of about 60° C., and 84.3 L of deaerated tap water was added dropwise thereto at the same temperature for about 1 hour. Thereafter, the resulting mixture was stirred at the same temperature for about 1 hour. The mixture was cooled to an internal temperature of about 25° C. and then stirred at the same temperature for about 0.5 hours. Subsequently, the reaction solution was allowed to stand overnight.

The precipitated crystals were filtered and washed with 31.6 L of a mixed solvent of deaerated N,N-dimethylacetamide and tap water (10:8). The obtained wet crystals were dried at an external temperature of 40° C. under reduced pressure to obtain 8.80 Kg of crude methyl 4-[(E)-2-(4-aminophenyl)ethenyl]benzoate (yield: 93.4%).

17.06 Kg of the thus synthesized crude methyl 4-[(E)-2-(4-aminophenyl)ethenyl]benzoate was dissolved in 198.2 Kg of N,N-dimethylacetamide while warmed to about 60° C. 168.6 L of water was added dropwise thereto at the same temperature, over 1 hour, and then the resulting mixture was stirred at the same temperature for 1 hour. The mixture was cooled to 30° C. or lower and then stirred at 20° C. to 30° C. for about 0.5 hours. Thereafter, the precipitated crystals were filtered and washed with 63.2 L of methanol.

The obtained wet crystals were dried at an external temperature of about 40° C. under reduced pressure to obtain 16.44 Kg of methyl 4-[(E)-2-(4-aminophenyl)ethenyl]benzoate (yield: 96.4%).

Melting point: 218.2° C. $^1$H-NMR (500 MHz, DMSO-$d_6$) δ: 3.836 (3H, s), 5.426 (2H, s), 6.575 (2H, d, J=7.0 Hz), 6.960 (1H, d, J=16.5 Hz), 7.233 (1H, d, J=16.5 Hz), 7.323 (2H, 1H, J=8.5 Hz), 7.616 (2H, d, J=8.5 Hz), 7.896 (2H, d, J=8.5 Hz).

Example 4

Methyl 4-[(E)-2-(4-aminophenyl)ethenyl]benzoate (6-m)

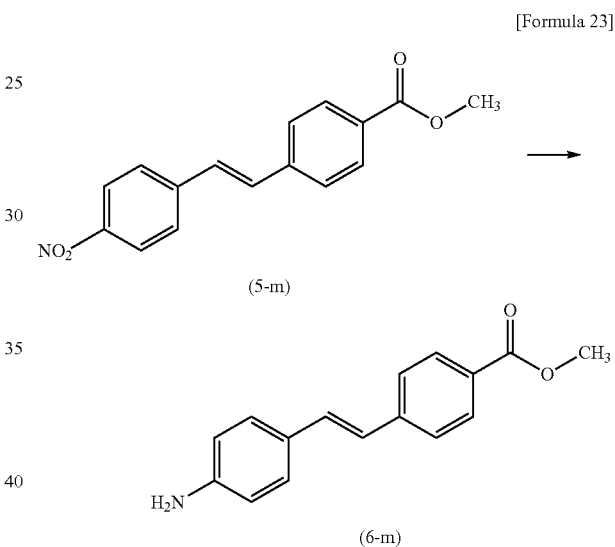

Under a nitrogen atmosphere, 5.0 g of the methyl 4-[(E)-2-(4-nitrophenyl)ethenyl]benzoate produced in Example 2 (17.65 mmol basis), 35 mL of N,N-dimethylacetamide, 328 mg of 3% platinum-0.3% iron carbon (manufactured by Evonik, 61.9% wet product), and 0.25 mL dimethyl sulfoxide were added. After replacement by a hydrogen atmosphere, the resulting mixture was stirred under a hydrogen pressure of 0.5 MPaG at 20° C. to 55° C. for about 5 hours. After replacement by a nitrogen atmosphere, the mixture was cooled to about 25° C., and the catalyst was filtered. The catalyst was washed with 15 mL of N,N-dimethylacetamide, and then the filtrates were combined. The obtained solution was heated to an internal temperature of about 60° C., and a solution of 0.5 g of sodium hydrogen sulfite in water (25 mL) was added dropwise thereto at the same temperature over about 1 hour. Thereafter, the resulting mixture was stirred at the same temperature for about 1 hour. The mixture was cooled to an internal temperature of about 40° C. and then stirred at the same temperature for about 1 hour. The precipitated crystals were filtered and washed with 20 mL of a mixed solvent of N,N-dimethylacetamide and tap water (2:1) and then with 20 mL of methanol. The obtained wet crystals were dried at an external temperature of 40° C. under reduced pressure to obtain 4.26 g of the title compound (yield: 95.3%).

Example 5

Methyl 4-[2-(4-aminophenyl)ethyl]benzoate (7-m)

[Formula 24]

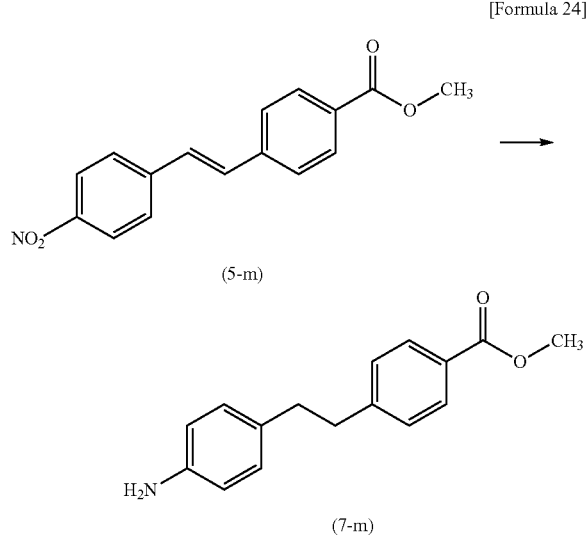

Under a nitrogen atmosphere, 30 g of the methyl 4-[(E)-2-(4-nitrophenyl)ethenyl]benzoate produced in Example 1 (0.037 mol basis), 150 mL of N,N-dimethylformamide, 450 mL of tetrahydrofuran, and 6.34 g of 5% palladium carbon (53% wet product) were added. After replacement by a hydrogen atmosphere, the resulting mixture was stirred under a hydrogen pressure of 0.3 MPaG at 50° C. for about 3 hours. After replacement by a nitrogen atmosphere, the mixture was cooled to about 25° C., and allowed to stand overnight. Tetrahydrofuran was distilled away under reduced pressure, and 300 mL of tap water was added to the residue. The precipitated crystals were filtered and washed with 60 mL of 90% aqueous N,N-dimethylformamide and 60 mL of tap water. The obtained wet crystals were dried at an external temperature of 50° C. under reduced pressure to obtain 24.99 g of methyl 4-[2-(4-aminophenyl)ethyl]benzoate (yield: 92.4%). Melting point: 121.8° C. $^1$H-NMR (500 MHz, CD$_3$OD) δ: 2.795 (2H, dd, J=6.0, 8.5 Hz), 2.905 (2H, dd, J=6.0, 8.5 Hz), 6.638 (2H, ddd, J=2.0, 2.5, 8.5 Hz), 6.887 (2H, ddd, J=2.0, 2.5, 8.5 Hz), 7.237 (2H, ddd, J=2.0, 3.0, 8.5 Hz), 7.878 (2H, ddd, J=2.0, 3.0, 8.5 Hz).

Example 6

Methyl 4-[(E)-2-(4-{[2-nitro-5-(piperidin-1-yl)benzoyl]amino}phenyl)ethenyl]benzoate (9-m)

[Formula 25]

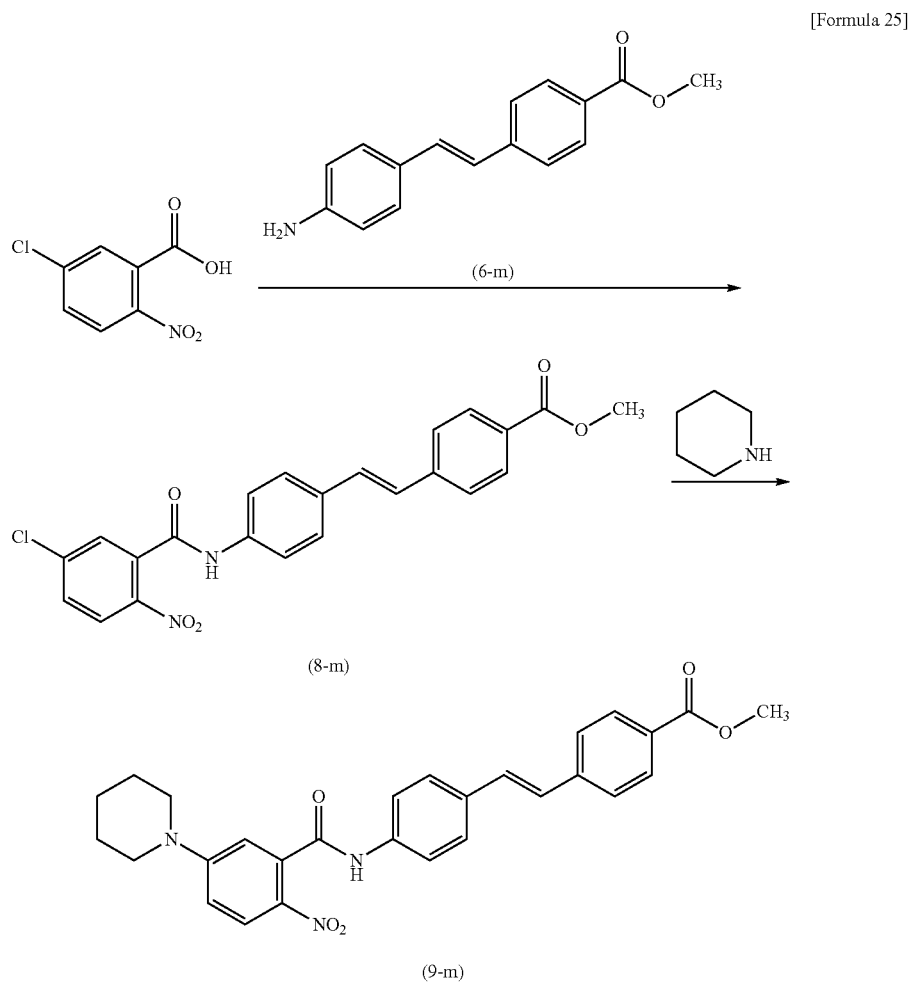

Under a nitrogen atmosphere, 11.46 Kg (1.4 equivalents) of oxalyl chloride was added dropwise to a mixed solution of 14.18 Kg (1.1 equivalents) of 5-chloro-2-nitrobenzoic acid, 70.5 Kg of toluene and 0.15 Kg of N,N-dimethylacetamide at an internal temperature of about 15° C. The present reaction solution was warmed to about 67° C. and stirred for 2.5 hours, and then concentrated under reduced pressure to a liquid volume of 40.5 L to obtain a solution of 5-chloro-2-nitrobenzoyl chloride in toluene.

On the other hand, under a nitrogen atmosphere, the solution of 5-chloro-2-nitrobenzoyl chloride in toluene obtained above was added dropwise to a mixed solution of 16.2 Kg (0.064 kmol) of the methyl 4-[(E)-2-(4-aminophenyl)ethenyl]benzoate produced in Example 3 or Example 4, 16.18 Kg (2.5 equivalents) of triethylamine, and 216.3 Kg of tetrahydrofuran at an internal temperature of 16° C. to 33° C., followed by fully washing with 7.05 Kg of toluene. The resulting mixture was stirred at about 50° C. for 2 hours, and then 60.9 Kg of N,N-dimethylacetamide was added thereto, and the resulting mixture was concentrated under reduced pressure to a liquid volume of 162 L or less. This operation was carried out three times to obtain a solution of methyl 4-[(E)-2-(4-{[5-chloro-2-nitrobenzoyl]amino}phenyl)ethenyl]benzoate in N,N-dimethylacetamide.

To the present solution, 27.30 Kg (5.0 equivalents) of piperidine was added, and then the resulting mixture was stirred at an internal temperature of 95° C. to 98° C. for 3 hours. The mixture was cooled to an internal temperature of 50° C., and then 128.0 Kg of acetone was added thereto. 130 mL of water was added dropwise thereto at an internal temperature of about 50° C. over 1 hour. The resulting mixture was cooled to an internal temperature of about 30° C. and then stirred at the same temperature for 30 minutes. Thereafter, the precipitated crystals were filtered.

The crystals were successively washed with 81.0 L of 50% methanol-water and then with 81.0 L of methanol. The obtained wet crystals were dried at an external temperature of 40° C. under reduced pressure to obtain 27.96 Kg of methyl 4-[(E)-2-(4-{[2-nitro-5-(piperidin-1-yl)benzoyl]amino}phenyl)ethenyl]benzoate as yellow crystals (yield: 90.0%).

Melting point: 248.4° C. (dec.). $^1$H-NMR (500 MHz, DMSO-$d_6$) δ: 1.578 (4H, m), 1.638 (2H, m), 3.543 (4H, m), 3.857 (3H, s), 7.007 (1H, d, J=3.0 Hz), 7.048 (1H, dd, J=3.0, 9.5 Hz), 7.268 (1H, d, J=16.0 Hz), 7.402 (1H, d, J=16.0 Hz), 7.639 (2H, d, J=9.5 Hz), 7.719 (4H, m), 7.948 (2H, d, J=8.0 Hz), 8.043 (1H, d, J=9.5 Hz), 10.534 (1H, s).

Example 7

Methyl 4-[2-(4-{[2-amino-5-(piperidin-1-yl)benzoyl]amino}phenyl)ethyl]benzoate hydrochloride (10-m)

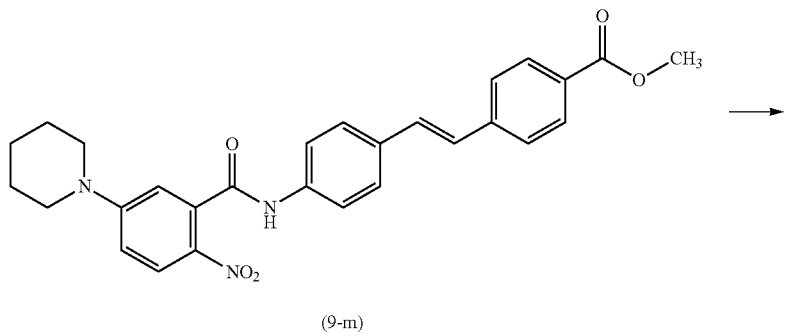

(9-m)

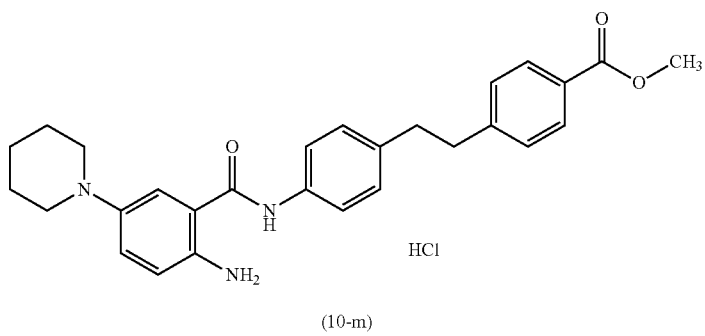

(10-m)

Under a nitrogen atmosphere, 13.86 Kg of the methyl 4-[(E)-2-(4-{[2-nitro-5-(piperidin-1-yl)benzoyl]amino}phenyl)ethenyl]benzoate produced in Example 6 (0.029 kmol basis), 65.1 Kg of N,N-dimethylacetamide, 62.4 Kg of ethyl acetate, and 1.54 Kg of 5% palladium carbon (PE type manufactured by N. E. Chem cat, 55.38% wet product) were added.

The resulting mixture was heated to an internal temperature of about 50° C., followed by replacement by a hydrogen atmosphere. The mixture was stirred under a hydrogen pressure of 0.5 MPaG at 50° C. to 60° C. for about 2 hours.

After replacement by a nitrogen atmosphere, the catalyst was filtered. The catalyst was washed with 37.4 Kg of ethyl acetate, and then the filtrates were combined.

49.9 Kg of ethyl acetate was added thereto, and a solution of 4 N hydrogen chloride in ethyl acetate (6.5 kg) was added dropwise to the reaction solution at an internal temperature of about 40° C. over about 1.5 hours. Crystallization was confirmed, and the resulting mixture was stirred at the same temperature for 30 minutes and then cooled to an internal temperature of 30° C. The mixture was stirred at 25° C. to 30° C. for 45 minutes, and then the precipitated crystals were filtered and washed with 37.4 Kg of ethyl acetate. The obtained wet crystals were dried at an external temperature of 40° C. under reduced pressure to obtain 13.60 Kg of methyl 4-[2-(4-{[2-amino-5-(piperidin-1-yl)benzoyl]amino}phenyl)ethyl]benzoate hydrochloride as fine yellow crystals (yield: 96.4%).

Melting point: 239.5° C. (dec.). $^1$H-NMR (500 MHz, DMSO-$d_6$) δ: 1.490-2.100 (6H, m), 2.895 (1H, d, J=14.5 Hz), 2.903 (1H, dd, J=2.5, 9.0 Hz), 2.955 (1H, dd, J=2.5, 9.0 Hz), 2.968 (1H, d, J=14.5 Hz), 3.477 (4H, br s), 6.627 (2H, br s), 6.853 (1H, d, J=8.5 Hz), 7.185 (2H, d, J=8.5 Hz), 7.362 (2H, d, J=8.0 Hz), 7.538 (2H, d, J=6.5 Hz), 7.593 (1H, m), 7.864 (2H, dd, J=1.5, 6.5 Hz), 7.953 (1H, br s), 10.179 (1H, s), 11.865 (1H, br s).

Example 8

Methyl 4-[2-(4-{[2-amino-5-(piperidin-1-yl)benzoyl]amino}phenyl)ethyl]benzoate (11-m)

Under a nitrogen atmosphere, 50.0 g of the methyl 4-[(E)-2-(4-{[2-nitro-5-(piperidin-1-yl)benzoyl]amino}phenyl)ethenyl]benzoate produced in Example 6 (0.103 mol basis), 250 mL of N,N-dimethylacetamide, 250 mL of ethyl acetate, and 5.60 g of 5% palladium carbon (PE type manufactured by N. E. Chem cat, 55.38% wet product) were added.

The resulting mixture was heated to an internal temperature of about 50° C., followed by replacement by a hydrogen atmosphere. The mixture was stirred under a hydrogen pressure of 0.5 MPaG at 50° C. to 60° C. for about 4 hours.

After replacement by a nitrogen atmosphere, the catalyst was filtered. The catalyst was washed with 150 ml of ethyl acetate, and then the filtrates were combined. The present filtrate was concentrated under reduced pressure and dissolved in 500 mL of ethyl acetate, and then washed with 300 mL of water three times. The organic layer was concentrated under reduced pressure.

The resulting concentrate was dissolved in 250 mL of acetonitrile, and then the resulting solution was concentrated under reduced pressure. The resulting concentrate was dissolved in 100 mL of acetonitrile, and then the resulting solution was inoculated with the seed crystals produced in Example 9. The solution was stirred under ice cooling for 15 minutes, and then the precipitated crystals were filtered and washed with 50 mL of cold acetonitrile. The obtained wet crystals were dried at room temperature under reduced pressure to obtain 38.16 g of methyl 4-[2-(4-{[2-amino-5-(piperidin-1-yl)benzoyl]amino}phenyl)ethyl]benzoate as dark greenish yellow crystals (yield: 81.0%).

Melting point: 115.6° C. $^1$H-NMR was identical to that of the compound of Example 9.

[Formula 27]

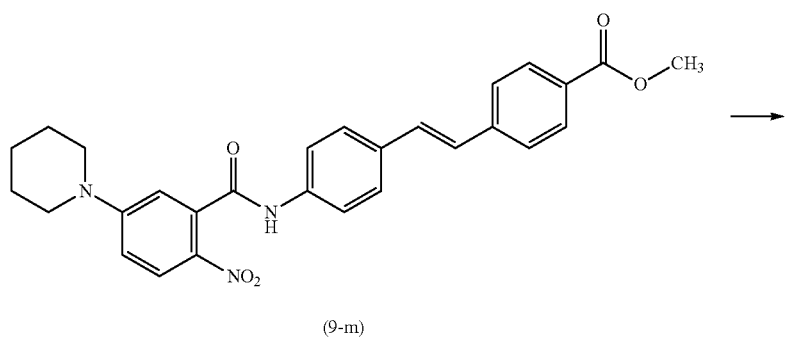

(9-m)

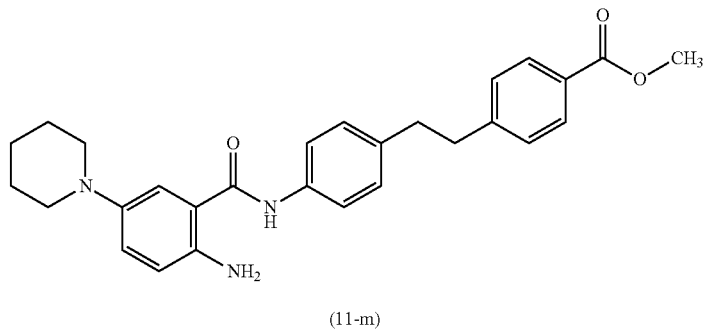

(11-m)

Example 9

Seed Crystals of methyl 4-[2-(4-{[2-amino-5-(piperidin-1-yl)benzoyl]amino}phenyl)ethyl]benzoate (11-m)

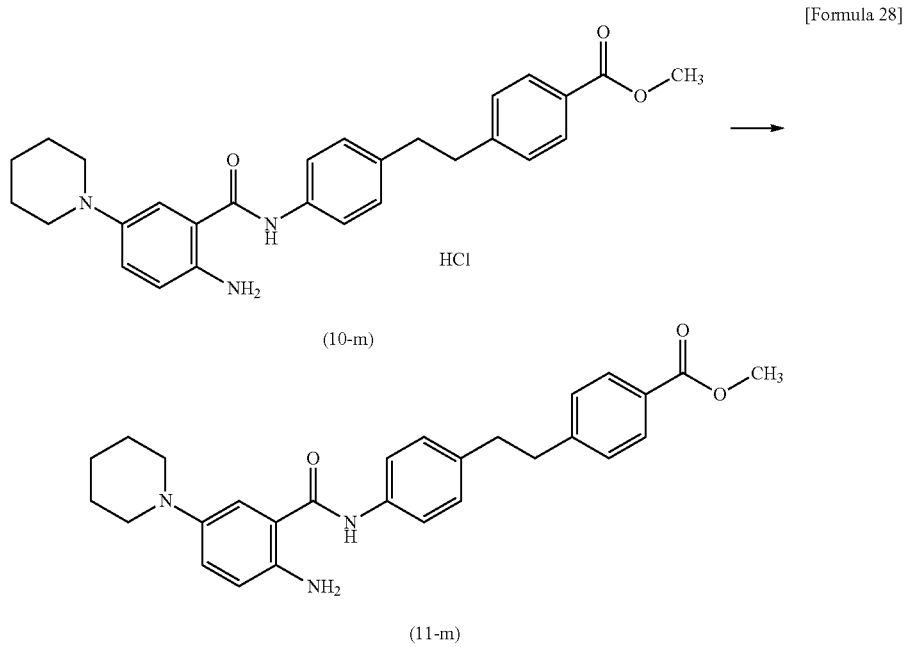

30.0 g (0.061 mol) of the methyl 4-[2-(4-{[2-amino-5-(piperidin-1-yl)benzoyl]amino}phenyl)ethyl]benzoate hydrochloride produced in Example 7 and 450 mL of ethyl acetate were added to a solution of 40.0 g of potassium bicarbonate in water (227 mL), and the resulting mixture was stirred at room temperature for about 30 minutes. After separating, the organic layer was washed with 150 mL of water, and concentrated under reduced pressure. The resulting concentrate was dissolved in 90 mL of acetonitrile and concentrated under reduced pressure. 90 mL of toluene was added thereto, and the resulting mixture was concentrated to dryness under reduced pressure. To the precipitated crystals, 30 mL of acetonitrile was added, and the resulting mixture was stirred under ice cooling for about 30 minutes. Thereafter, the crystals were filtered and washed with 30 mL of cold acetonitrile. The obtained wet crystals were dried at room temperature under reduced pressure to obtain 22.98 g of methyl 4-[2-(4-{[2-amino-5-(piperidin-1-yl)benzoyl]amino}phenyl)ethyl]benzoate as yellow crystals (yield: 82.7%).

Melting point: 117.0° C. $^1$H-NMR (500 MHz, DMSO-d$_6$) δ: 1.483 (2H, m), 1.628 (4H, m), 2.860-2.960 (8H, m), 3.828 (3H, s), 5.729 (2H, s), 6.667 (1H, d, J=8.5 Hz), 6.942 (1H, d, J=9.0 Hz), 7.092 (1H, s), 7.152 (2H, d, J=7.5.0 Hz), 7.363 (2H, d, J=7.0 Hz), 7.559 (2H, d, J=7.0 Hz), 7.864 (2H, d, J=7.0 Hz), 9.897 (1H, s).

Example 10

Methyl 4-{2-[4-({2-{[trans-4-(ethoxycarbonyl)cyclohexyl](ethyl)sulfamoyl}benzoyl)amino]-5-(piperidin-1-yl)benzoyl]amino}phenyl)ethyl]benzoate (12-me)

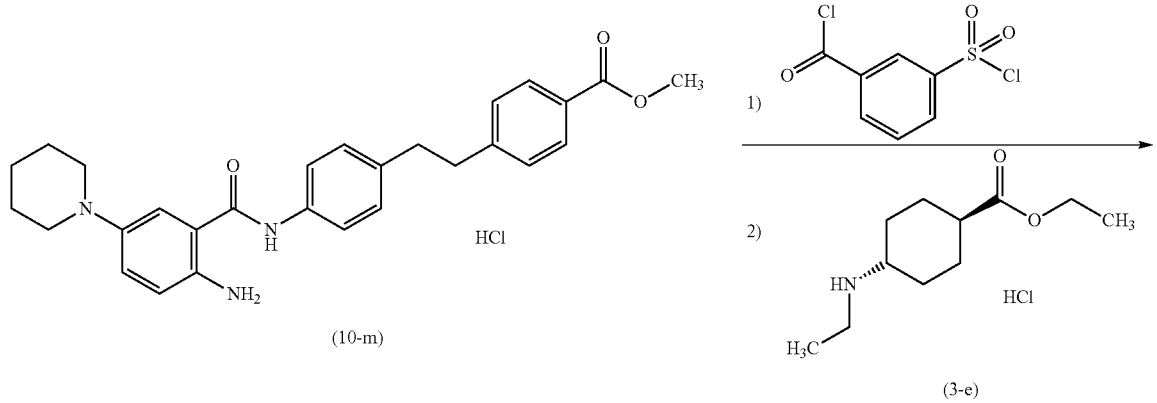

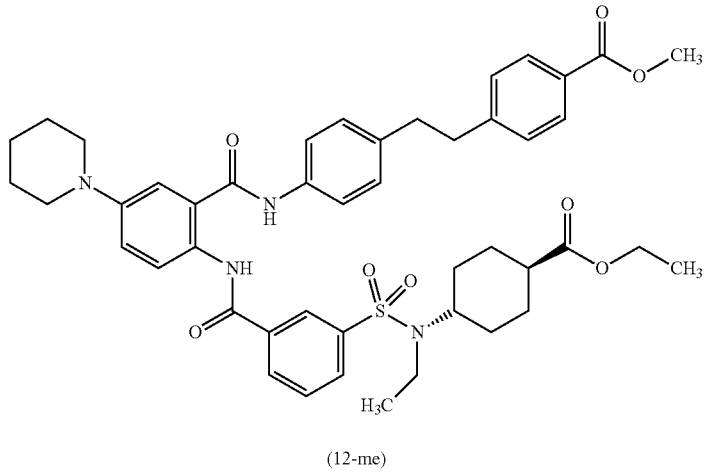

(12-me)

Under a nitrogen atmosphere, a mixed solution of 240 L of ethyl acetate, 20.00 Kg (0.040 kmol) of the methyl 4-[2-(4-{[2-amino-5-(piperidin-1-yl)benzoyl]amino}phenyl)ethyl]benzoate hydrochloride produced by the same production method as that of Example 7, 152 L of water, and 26.60 Kg of potassium bicarbonate was stirred at room temperature for about 1 hour.

After separating, the organic layer was washed with 180 L of water and 20.00 Kg of crude salt. After separating, the organic layer was concentrated under reduced pressure to a liquid volume of 45 L. 200 L of acetonitrile was added thereto, and the resulting mixture was concentrated under reduced pressure to a liquid volume of 45 L. This operation was carried out twice, and 15 L of acetonitrile was added thereto. 60 L of tetrahydrofuran was added thereto to obtain a solution of methyl 4-[2-(4-{[2-amino-5-(piperidin-1-yl)benzoyl]amino}phenyl)ethyl]benzoate in acetonitrile-tetrahydrofuran.

On the other hand, under a nitrogen atmosphere, 16.19 Kg (3.0 equivalents) of oxalyl chloride was added dropwise to a mixed solution of 96 L of ethyl acetate, 9.53 Kg (1.05 equivalents) of monosodium 3-sulfobenzoate, and 94 g of N,N-dimethylformamide. The resulting mixture was gradually heated and was heated at an internal temperature of 60° C. to 67° C. for 5 hours. After cooling, the mixture was concentrated under reduced pressure to a liquid volume of 25 L. 96 L of acetonitrile was added thereto, and the resulting mixture was concentrated under reduced pressure to a liquid volume of 25 L. This operation was carried out four times. 4 L of acetonitrile was added to the resulting concentrate to obtain a solution of 3-(chlorosulfonyl)benzoyl chloride in acetonitrile.

100 L of acetonitrile and 40 L of tetrahydrofuran were added to the solution, and the solution of methyl 4-[2-(4-{[2-amino-5-(piperidin-1-yl)benzoyl]amino}phenyl)ethyl]benzoate in acetonitrile-tetrahydrofuran obtained above was added dropwise thereto at an internal temperature of 22° C. to 27° C. After fully washing with 50 L of tetrahydrofuran, the resulting mixture was stirred at an internal temperature of 24° C. to 25° C. for 4 hours.

11.45 Kg (1.2 equivalents) of the ethyl trans-4-ethylaminocyclohexanecarboxylate hydrochloride produced in Example 13 was added to the mixture, and the resulting mixture was cooled to an internal temperature of 9° C.

4.40 Kg (1.0 equivalent) of trimethylsilyl chloride was added thereto, and 24.58 Kg (6.0 equivalents) of triethylamine was added dropwise thereto at an internal temperature of 5° C. to 9° C. over about 30 minutes. The resulting mixture was stirred at an internal temperature of 9° C. to 14° C. for about 3 hours. 150 L of water was added dropwise thereto at an internal temperature of 14° C. to 17° C. over 8 minutes, and the resulting mixture was stirred at an internal temperature of 17° C. to 20° C. for 12 hours. Thereafter, the precipitated crystals were filtered and washed with a mixed solution of 30 L of tetrahydrofuran and 30 L of water.

The obtained wet crystals were dried at an external temperature of 50° C. under reduced pressure to obtain 30.84 Kg of methyl 4-{2-[4-({2-{[trans-4-(ethoxycarbonyl)cyclohexyl](ethyl)sulfamoyl}benzoyl)amino]-5-(piperidin-1-yl)benzoyl]amino}phenyl)ethyl]benzoate (yield: 92.6%).

Melting point: 187.5° C. $^1$H-NMR (500 MHz, DMSO-$d_6$) δ: 1.119 (6H, m), 1.332 (2H, m), 1.400-1.500 (4H, m), 1.561 (2H, m), 1.651 (4H, m), 1.824 (2H, d, J=12.0 Hz), 2.156 (1H, m), 2.898 (2H, m), 2.946 (2H, m), 3.212 (6H, m), 3.605 (2H, m), 3.829 (3H, s), 3.985 (2H, ddd, J=3.0, 7.0, 10.0 Hz), 7.200-7.225 (3H, m), 7.330 (1H, d, J=3.0 Hz), 7.359 (2H, dd, J=2.5, 8.5 Hz), 7.753 (1H, dt, J=3.0, 8.0 Hz), 7.857 (2H, ddd, 2.5, 4.5, 8.5 Hz), 8.037 (1H, d, J=8.0 Hz), 8.115 (1H, dt, J=1.0, 7.0 Hz), 8.271 (1H, dd, J=2.0, 3.0 Hz), 10.374 (1H, s), 11.389 (1H, s).

Example 11

4-[2-(4-{[2-({3-[(trans-4-carbocyclohexyl) (ethyl) sulfamoyl]}benzoyl}amino)-5-(piperidin-1-yl)benzoyl]amino}phenyl)ethyl]benzoic acid (13)

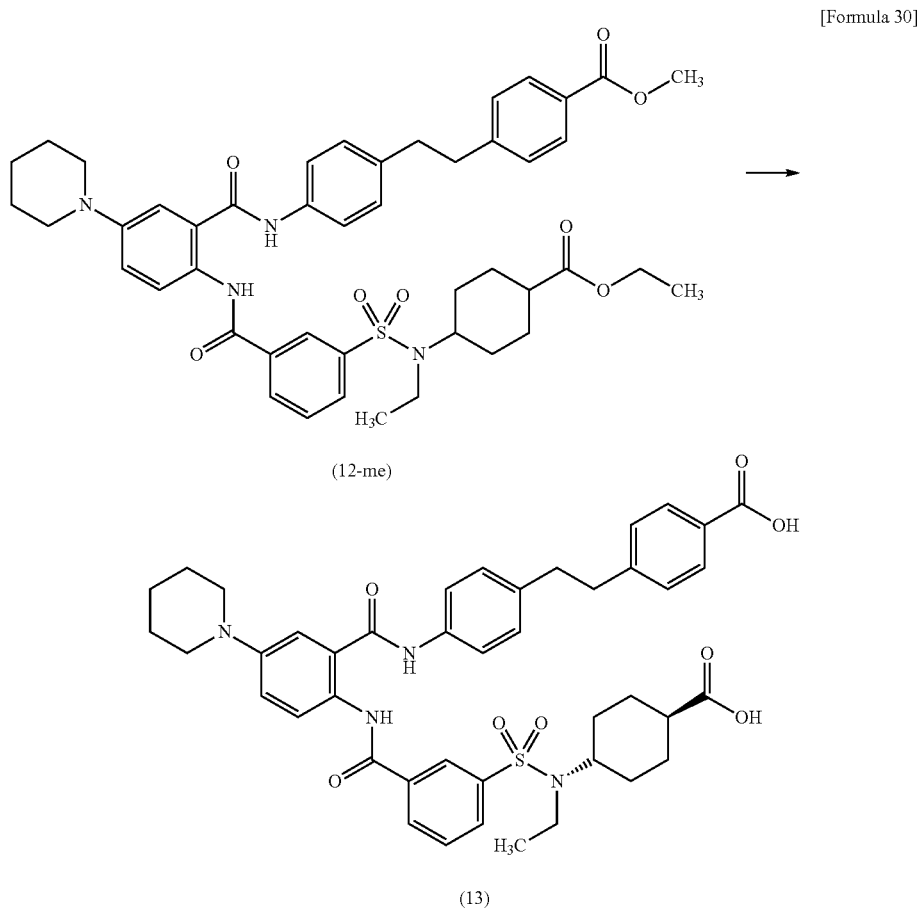

[Formula 30]

Under a nitrogen atmosphere, a mixed solution of 75 L of methanol, 15.00 Kg (0.018 kmol) of the methyl 4-{2-[4-({2-{[trans-4-(ethoxycarbonyl)cyclohexyl](ethyl) sulfamoyl}benzoyl)amino]-5-(piperidin-1-yl)benzoyl] amino}phenyl)ethyl]benzoate produced in Example 10, 75 L of tetrahydrofuran, 9 L of water, and 11.66 Kg (4.0 equivalents) of a 25% aqueous solution of sodium hydroxide was stirred at an internal temperature of 45° C. to 51° C. for 4 hours.

After cooling, 13.3 L of 6 N hydrochloric acid was added to the mixed solution to adjust the pH to 4.75. After stirring for 3.5 hours, 38 mL of 6 N hydrochloric acid was added thereto to adjust the pH to 5.0. 120 L of water was added thereto, and the resulting mixture was stirred at room temperature overnight.

The precipitated crystals were filtered and successively washed with a mixed solution of 23 L of methanol and 23 L of water and then with 45 L of methanol. The obtained wet crystals were dried at an external temperature of 40° C. under reduced pressure to obtain 13.86 Kg of 4-[2-(4-{[2-({3-[(trans-4-carbocyclohexyl) (ethyl)sulfamoyl] }benzoyl}amino)-5-(piperidin-1-yl)benzoyl]amino}phenyl) ethyl]benzoic acid as light yellow crystals (yield: 97.4%). Melting point: 236.5° C. $^1$H-NMR (500 MHz, DMSO-$d_6$) δ: 1.133 (3H, t, J=7.0 Hz), 1.304 (2H, m), 1.400-1.510 (4H, m), 1.523 (2H, m), 1.656 (4H, m), 1.841 (2H, br d, J=11.5 Hz), 2.079 (1H, tt, J=3.0, 12.0 Hz), 2.880 (1H, d, J=2.5, 9.0 Hz), 2.894 (1H, d, J=8.0 Hz), 2.940 (1H, d, J=8.0 Hz), 2.955 (1H, dd, J=2.5, 9.0 Hz), 3.220 (6H, m), 3.600 (1H, m), 7.182 (3H, d, J=8.5 Hz), 7.335 (3H, d, J=7.5 Hz), 7.583 (2H, d, J=8.5 Hz), 7.758 (1H, t, J=8.0 Hz), 7.841 (2H, d, 8.0 Hz), 8.036 (1H, d, J=8.5 Hz), 8.107 (1H, d, J=8.0 Hz), 8.124 (1H, d, J=8.5 Hz), 8.272 (1H, s), 10.376 (1H, s), 11.383 (1H, s), 12.490 (2H, br s).

Example 12

Method for Synthesizing ethyl 4-ethylaminocyclohexanecarboxylate hydrochloride (2-e)

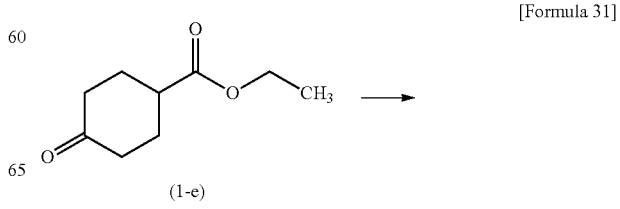

[Formula 31]

-continued

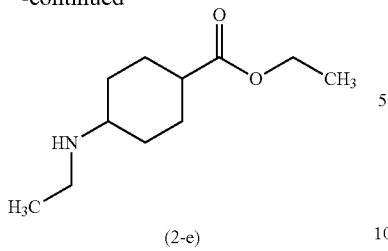

(2-e)

Reductive Amination Method 17.90 Kg (0.105 kmol) of ethyl 4-oxocyclohexanecarboxylate, 90 L of ethanol, 1.00 Kg of 5% palladium carbon (a product with a water content of 55.38%), and 13.69 Kg of a 70% aqueous solution of ethylamine were added to a reaction vessel, and the resulting mixture was warmed to about 40° C. under a nitrogen atmosphere. After the reaction vessel was purged with hydrogen, the mixture was stirred under a hydrogen pressure of 0.3 MPaG at 39° C. to 50° C. for 2.25 hours.

After cooling to about 30° C., the reaction vessel was purged with nitrogen, and the catalyst was filtered. The catalyst was washed with 36 L of ethanol, and the filtrates were combined. The obtained filtrate was concentrated under reduced pressure to a liquid volume of 45 L. 90 L of xylene was added thereto, and the resulting mixture was concentrated under reduced pressure to a liquid volume of 54 L. 90 L of xylene was added thereto again, and the resulting mixture was concentrated under reduced pressure to a liquid volume of 39 L. Thereafter, 51 L of xylene was added thereto to adjust the internal volume to 90 L to obtain a solution of ethyl 4-ethylaminocyclohexanecarboxylate in xylene (trans isomer content: 10.30 Kg, trans:cis=about 1:1). Analysis conditions—(GC) retention time: trans isomer 4.6 min, cis isomer 4.5 min, column: CP, CP-SIL 8CB FOR AMINES, 0.25 MM*30M, DF=0.25, column temperature: 150° C. hold 3 min, 20° C./min→250° C., inlet temperature: 250° C., sample injection method: split method, split ratio: 1:20 (=column flow rate:split vent flow rate), purge flow rate: 3 mL/min, detector temperature: 250° C., $H_2$ flow rate: 30 mL/min, Air flow rate: 400 mL/min, make-up flow rate (He): 25 mL/min, analysis time: 8 min.

Example 13

Method for Synthesizing ethyl trans-4-ethylaminocyclohexanecarboxylate hydrochloride (3-e)

[Formula 32]

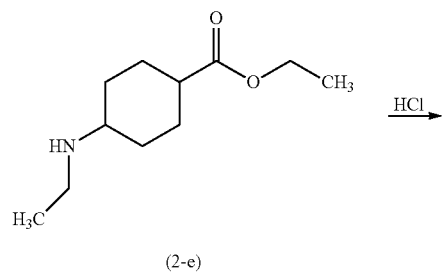

-continued

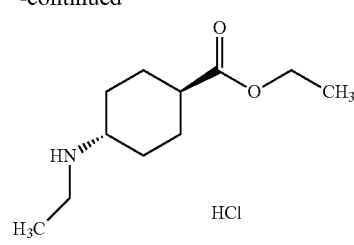

(3-e)

9.3 L (0.75 equivalents) of 4.16 N hydrogen chloride-ethyl acetate solution was added to the solution of ethyl 4-ethylaminocyclohexanecarboxylate in xylene, which had been prepared by the reductive amination method (10.30 Kg (NET amount) of ethyl trans-4-ethylaminocyclohexanecarboxylate, basis for calculation of the amounts added in the following operation), and the resulting mixture was heated to an internal temperature of 132° C. while the solvent was distilled away. Thereafter, the mixture was intermittently stirred at an internal temperature of 129° C. to 133° C. for 10 hours in total.

After cooling, 52 L of ethyl acetate was added to the mixture, and 3.17 L (0.26 equivalents) of a 4.24 N hydrogen chloride-ethyl acetate solution and 1.25 L (0.1 equivalents) of a 4.12 N hydrogen chloride-ethyl acetate solution were further added thereto at an internal temperature of 22° C. to 27° C. The resulting mixture was stirred at the same temperature for about 1.5 hours. The precipitated crystals were filtered and washed with a mixed solution of 15 L of xylene and 15 L of ethyl acetate. The obtained wet crystals were dried at an external temperature of 40° C. under reduced pressure to obtain 12.11 kg of ethyl trans-4-ethylaminocyclohexanecarboxylate hydrochloride (total yield from Example 12: 48.8%). Melting point: 140.6° C. $^1$H-NMR (500 MHz, DMSO-$d_6$) δ: 9.0 (2H, br s), 4.0 (2H, q, J=7.5 Hz), 2.95 (1H, tt, J=4.0, 11.5 Hz), 2.89 (2H, q, J=7.0 Hz), 2.23 (1H, tt, J=3.5, 11.5 Hz), 2.14-2.04 (2H, m), 2.02-1.88 (2H, m), 1.46-1.29 (4H, m), 1.20 (3H, t, J=7.5 Hz), 1.15 (3H, t, J=7.0 Hz), Analysis conditions—(GC) retention time: trans isomer 4.6 min, column: CP, CP-SIL 8CB FOR AMINES, 0.25 MM*30M, DF=0.25, column temperature: 150° C. hold 3 min, 20° C./min→250° C., inlet temperature: 250° C., sample injection method: split method, split ratio: 1:20 (=column flow rate:split vent flow rate), purge flow rate: 3 mL/min, detector temperature: 250° C., $H_2$ flow rate: 30 mL/min, Air flow rate: 400 mL/min, make-up flow rate (He): 25 mL/min, analysis time: 8 min.

Effect of Accelerating Reaction by Addition of Hydrogen Chloride

According to the operational method of Example 13, the reaction rate was compared between the case of adding hydrogen chloride during the reaction and the case of not adding hydrogen chloride during the reaction, and results are summarized in the following table.

It was found that the effect of accelerating the reaction rate is obtained by addition of hydrogen chloride.

TABLE 1

| entry | Solvent | Hydrogen chloride (equivalents) | Temperature (° C.) | Reaction completion time (h) | Trans isomer (%) | Cis isomer (%) | Lactam (%) |
|---|---|---|---|---|---|---|---|
| 1 | Xylene | 0 | 130 | 24 | 61.4 | 0.9 | 37.7 |
| 2 | Xylene | 0.6 | 130 | 9 | 61.9 | 1.2 | 37.0 |
| 3 | Xylene | 1 | 130 | 12 | 61.3 | 0.7 | 38.0 |

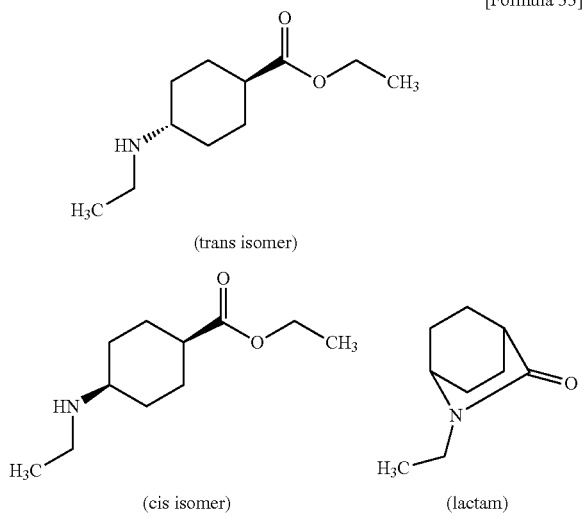

[Formula 33]

(trans isomer)

(cis isomer)    (lactam)

Change in Amount of Hydrochloric Acid and Quality During Crystallization

According to the operational method of Example 13, the relationship between the amount of hydrochloric acid during crystallization and the content of a product is summarized in the following table.

It was found that the amount of hydrochloric acid during crystallization has a great influence on the purity of the trans isomer.

TABLE 2

| entry | Total hydrogen chloride (equivalents) | Trans isomer (%) | Cis isomer (%) | Lactam (%) |
|---|---|---|---|---|
| Initial | — | 58.2 | 1.68 | 40.2 |
| 1 | 1.00 | 98.9 | 0.59 | 0.31 |
| 2 | 1.05 | 99.1 | 0.56 | 0.08 |
| 3 | 1.10 | 99.0 | 0.52 | 0.28 |
| 4 | 1.15 | 97.3 | 0.59 | 2.0 |
| 5 | 1.20 | 92.6 | 0.48 | 6.8 |

Effect of Adding Ethyl Acetate During Crystallization

Moreover, the effect obtained by addition of ethyl acetate during crystallization was studied and is summarized in the following table.

It was found that the amount of ethyl acetate during crystallization has an influence on the purity of the trans isomer.

TABLE 3

| entry | Amount of ethyl acetate added (fold, mL/g*) | Amount of hydrogen chloride added (eq) | Trans isomer (%) | Cis isomer (%) | Lactam (%) |
|---|---|---|---|---|---|
| Initial | — | — | 58.5 | 1.33 | 40.2 |
| 1 | 0 | 1.1 | 99.6 | 0.18 | 0.20 |
| 2 | 0 | 1.2 | 99.8 | 0.17 | 0.13 |
| 3 | 2.5 | 1 | 99.9 | 0.08 | 0.01 |
| 4 | 2.5 | 1.1 | 99.9 | 0.05 | 0.03 |
| 5 | 2.5 | 1.2 | 100 | 0.01 | trace |
| 6 | 5 | 1 | 99.9 | 0.06 | trace |
| 7 | 5 | 1.1 | 99.8 | 0.05 | 0.07 |
| 8 | 5 | 1.2 | 100 | 0.01 | trace |
| 9 | 10 | 1 | 99.9 | 0.04 | trace |
| 10 | 10 | 1.1 | 99.7 | 0.08 | 0.20 |

*Volume (mL) of ethyl acetate per g of ethyl trans-4-ethylaminocyclohexanecarboxylate Reference Example 1

Method for Synthesizing ethyl 4-ethylaminocyclohexanecarboxylate hydrochloride

[Formula 34]

Nuclear Reduction Method 7.0 g (0.042 mol) of ethyl 4-aminobenzoate, 70 mL of 2-propanol, 4.0 g (1 equivalent) of magnesium chloride, and 1.4 g of 5% rhodium carbon (a product with a water content of 51.8%) were added to a reaction vessel, and the resulting mixture was heated to about 80° C. under a nitrogen atmosphere. After the reaction vessel was purged with hydrogen, the mixture was stirred under a hydrogen pressure of 0.7 MPaG at the same temperature for 24 hours.

After cooling to about 30° C., the reaction vessel was purged with nitrogen, and the catalyst was filtered. The catalyst was washed with a small amount of 2-propanol, and then the filtrates were combined. The resulting filtrate was concentrated to dryness to obtain 6.55 g of ethyl 4-amino-cyclohexanecarboxylate hydrochloride (yield: 74.4%, trans:cis=about 1:3).

5.0 g (0.029 mol) of the present mixture, 50 mL of ethanol, 1.4 g of 5% rhodium carbon (a product with a water content of 51.8%), and 1.87 mL (1.5 equivalents) of acetaldehyde were added. After the reaction vessel was purged with hydrogen, the resulting mixture was stirred under a hydrogen pressure of 0.7 MPaG at the same temperature for 22 hours. 0.2 mL (0.1 equivalents) of acetaldehyde was added thereto, and the resulting mixture was further reacted for 16 hours.

The catalyst was filtered, and then washed with a small amount of ethanol and concentrated to dryness under reduced pressure. The crystals were stirred with a small amount of butyl acetate and then filtered. The obtained wet crystals were filtered with a small amount of butyl acetate to obtain 4.22 g of ethyl 4-ethylaminocyclohexanecarboxylate hydrochloride (trans isomer content: 0.34 g, trans:cis=about 1:10). Analysis conditions—(GC) retention time: trans isomer 4.6 min, column: CP, CP-SIL 8CB FOR AMINES, 0.25 MM*30M, DF=0.25, column temperature: 150° C. hold 3 min, 20° C./min→250° C., inlet temperature: 250° C., sample injection method: split method, split ratio: 1:20 (=column flow rate: split vent flow rate), purge flow rate: 3 mL/min, detector temperature: 250° C., H$_2$ flow rate: 30 mL/min, Air flow rate: 400 mL/min, make-up flow rate (He): 25 mL/min, analysis time: 8 min.

The invention claimed is:

1. A method for producing a compound represented by formula (13) or a pharmacologically acceptable salt thereof, the method comprising:
   (i) a step of
      1) reacting a compound represented by formula (10) or a compound represented by formula (11) with 3-(chlorosulfonyl)benzoyl chloride in a solvent to obtain a condensate, and then
      2) reacting the condensate with a compound represented by formula (3) in a solvent in the presence of a base to produce a compound represented by formula (12):

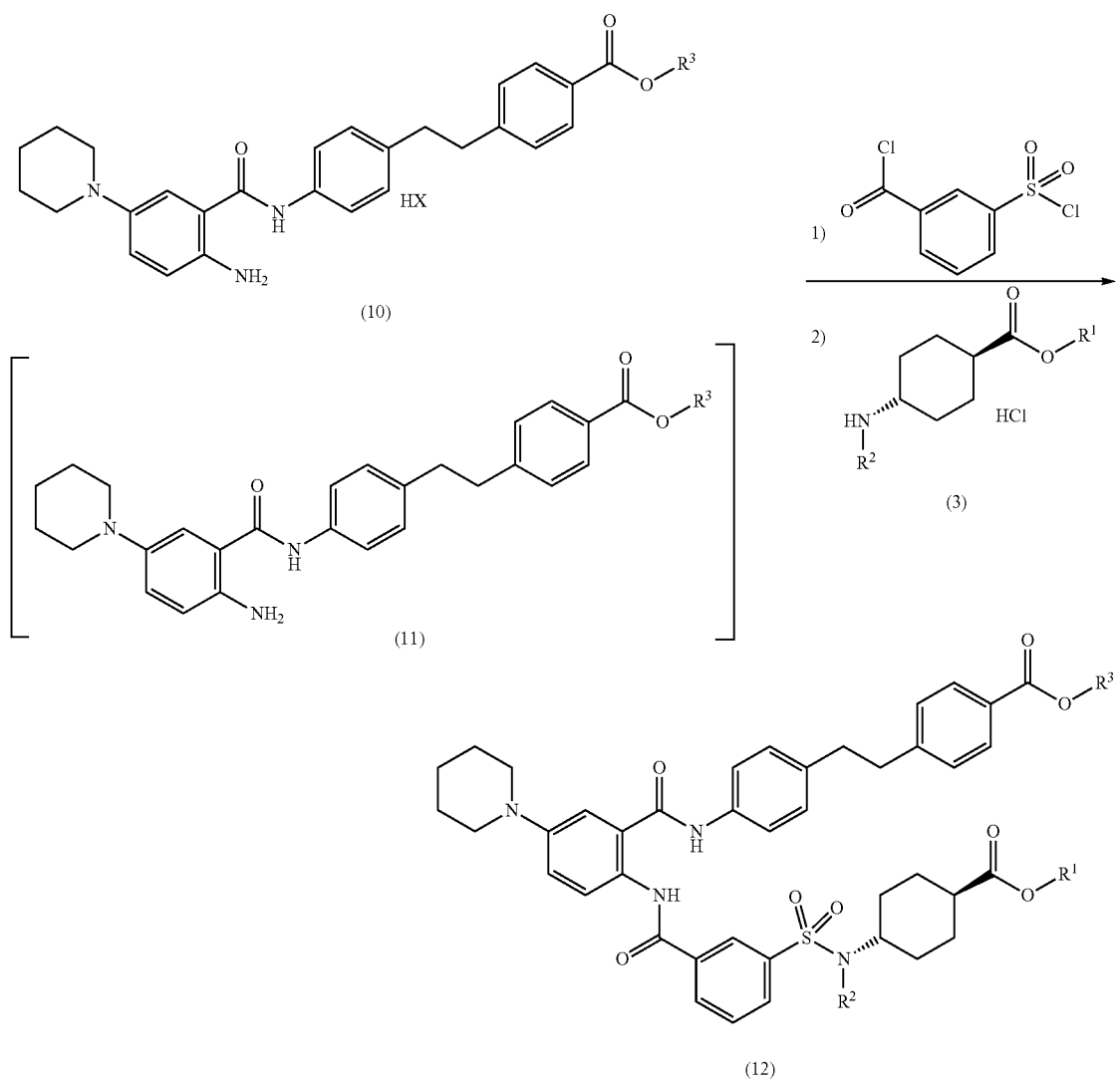

wherein R¹ represents a C1-C6 alkyl group, R² represents a C1-C6 alkyl group, R³ represents a C1-C6 alkyl group, and HX represents an acid; and (ii) a step of subjecting the compound represented by formula (12) produced in the previous step to a hydrolysis reaction in the presence of aqueous alkali in a solvent to produce a compound represented by formula (13):

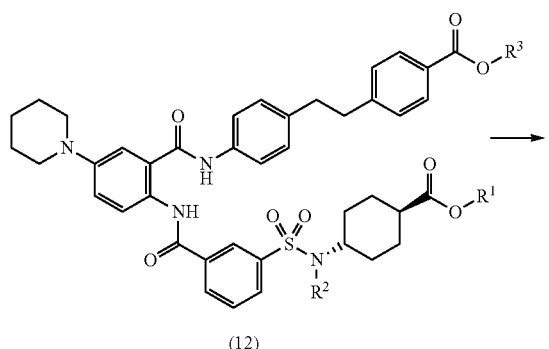

(12)

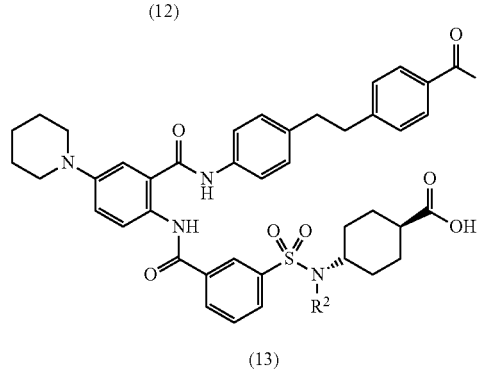

(13)

wherein R¹ represents a C1-C6 alkyl group, R² represents a C1-C6 alkyl group, and R³ represents a C1-C6 alkyl group.

2. The method according to claim 1, wherein in the step (i), 1), the solvent is N,N-dimethylacetamide, acetonitrile or acetonitrile-tetrahydrofuran; in the step (i), 2), the solvent is N,N-dimethylacetamide, tetrahydrofuran or acetonitrile-tetrahydrofuran, and the base is triethylamine, diethylisopropylamine, N-methylmorpholine, dimethylbenzylamine or cesium carbonate; and further a small amount of trimethylsilyl chloride is added.

3. The method according to claim 1, wherein in the step (ii), the aqueous alkali is an aqueous sodium hydroxide solution, and the solvent is N,N-dimethylacetamide, methanol-tetrahydrofuran (volume ratio: 1:0.5-2) or methanol-acetonitrile (volume ratio: 1:0.5-2).

4. A method for producing a compound represented by formula (10) or a compound represented by formula (11), the method comprising:

(i) a step of subjecting a compound represented by formula (6) to a condensation reaction with 5-chloro-2-nitrobenzoyl chloride in a solvent in the presence of a base to produce a compound represented by formula (8):

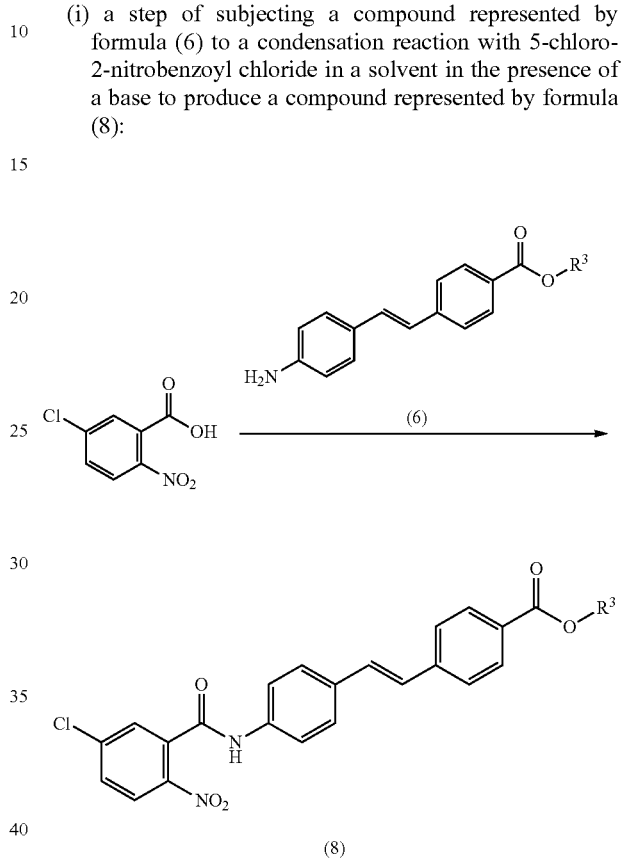

(8)

wherein R³ represents a C1-C6 alkyl group;

(ii) a step of reacting the compound represented by formula (8) produced in the previous step with piperidine in a solvent to produce a compound represented by formula (9):

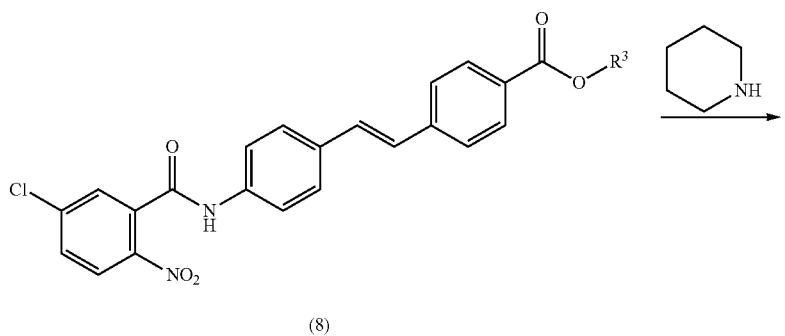

(8)

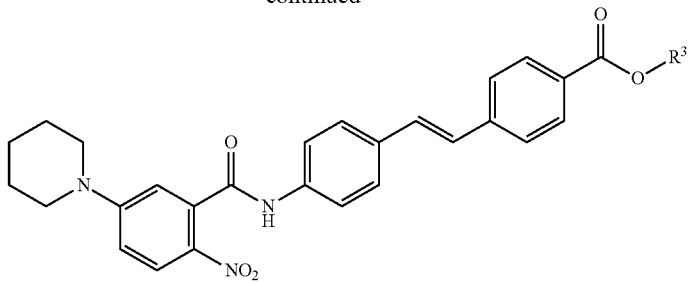

(9)

wherein R³ represents a C1-C6 alkyl group; and (iii) a step of treating the compound represented by formula (9) produced in the previous step with an acid in a solvent in the presence of a catalyst under a hydrogen atmosphere to produce a compound represented by formula (10); or a step of treating the compound represented by formula (9) produced in the previous step in a solvent in the presence of a catalyst under a hydrogen atmosphere to produce a compound represented by formula (11):

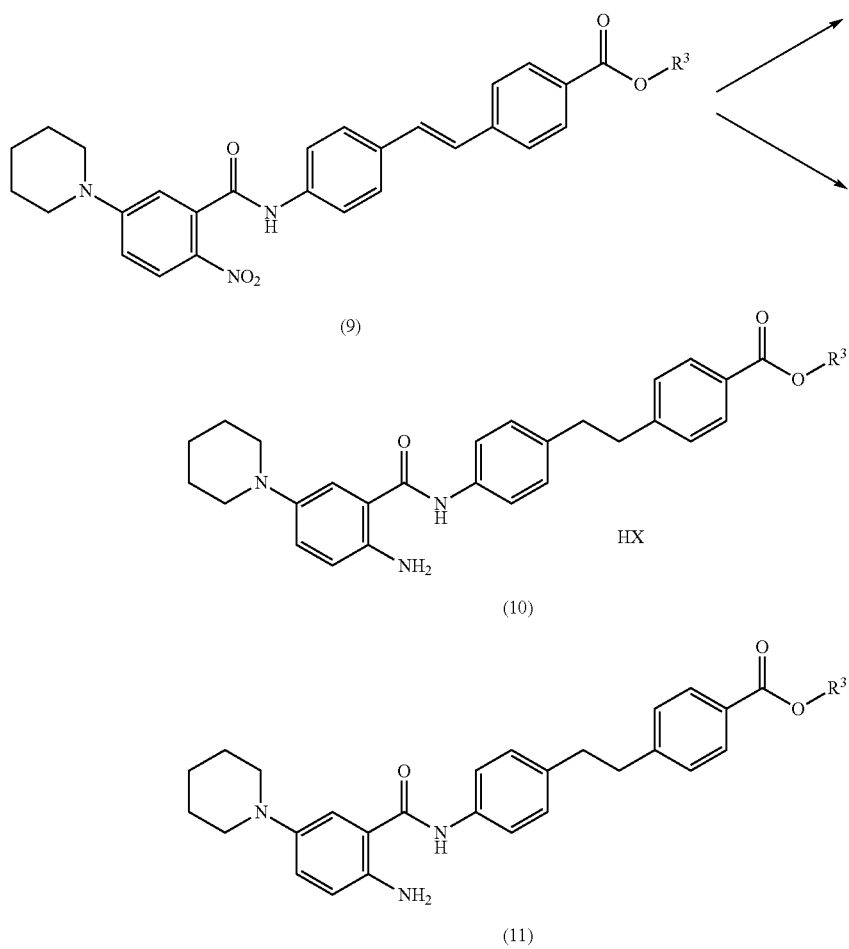

wherein R³ represents a C1-C6 alkyl group.

5. The method according to claim 4, wherein in the step (i), the 5-chloro-2-nitrobenzoyl chloride is produced by using thionyl chloride or oxalyl chloride as a chlorinating agent and also using N,N-dimethylacetamide or N,N-dimethylformamide as a catalyst, and the base and the solvent in the condensation reaction are pyridine, triethylamine or diisopropylamine, and tetrahydrofuran or tetrahydrofuran-toluene, respectively.

6. The method according to claim 4, wherein in the step (ii), the solvent is N,N-dimethylacetamide or N,N-dimethylformamide.

7. The method for producing a compound represented by formula (10) according to claim 4, wherein in the step (iii), the solvent is N,N-dimethylacetamide, or a mixed solvent of N,N-dimethylacetamide and ethyl acetate or methanol, and the catalyst is 5% palladium carbon, and the method further comprises a step of treating the obtained compound with hydrogen chloride.

8. A method for producing a compound represented by formula (6), the method comprising:
   (i) a step of reacting a compound represented by formula (4) with 1-methyl-4-nitrobenzene in a solvent in the presence of C1-C6 alkyl formate and a base to produce a compound represented by formula (5):

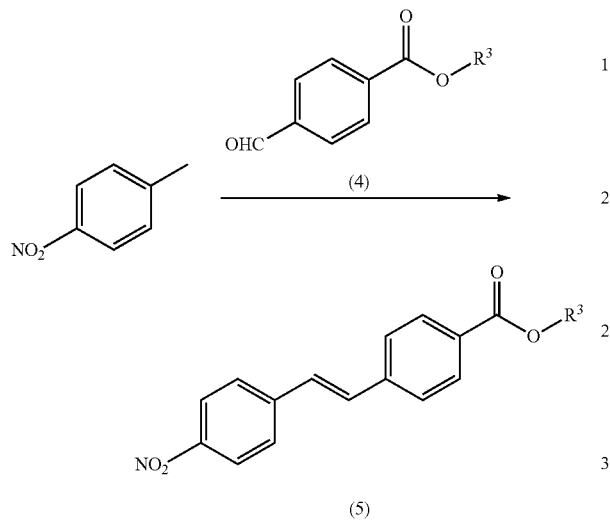

wherein $R^3$ represents a C1-C6 alkyl group; and
   (ii) a step of treating the compound represented by formula (5) produced in the previous step in a solvent in the presence of a hydrogenation catalyst and a catalyst poison under a hydrogen atmosphere to produce a compound represented by formula (6):

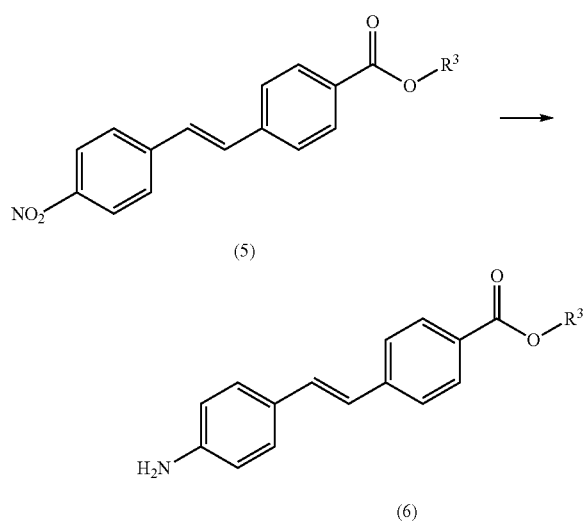

wherein $R^3$ represents a C1-C6 alkyl group.

9. The method according to claim 8, wherein in the step (i), the solvent is dimethyl sulfoxide or N,N-dimethylacetamide, the C1-C6 alkyl formate used is methyl formate, and the base is a solution of sodium methoxide in methanol.

10. The method according to claim 8, wherein in the step (ii), the solvent is N,N-dimethylacetamide or N,N-dimethylformamide, the hydrogenation catalyst is 3% platinum carbon, 0.8% platinum-0.3% molybdenum carbon, 3% platinum-0.3% iron carbon, or 1% platinum-0.1% copper carbon, and the catalyst poison is dimethyl sulfoxide.

11. A method for producing a compound represented by formula (3), the method comprising:
   (i) a step of treating a compound represented by formula (1) in a solvent in the presence of C1-C6 alkylamine and a palladium catalyst under a hydrogen atmosphere to obtain a compound represented by formula (2); and
   (ii) a step of heating and treating the compound represented by formula (2) produced in the previous step in a solvent in the presence of hydrogen chloride to obtain a compound represented by formula (3):

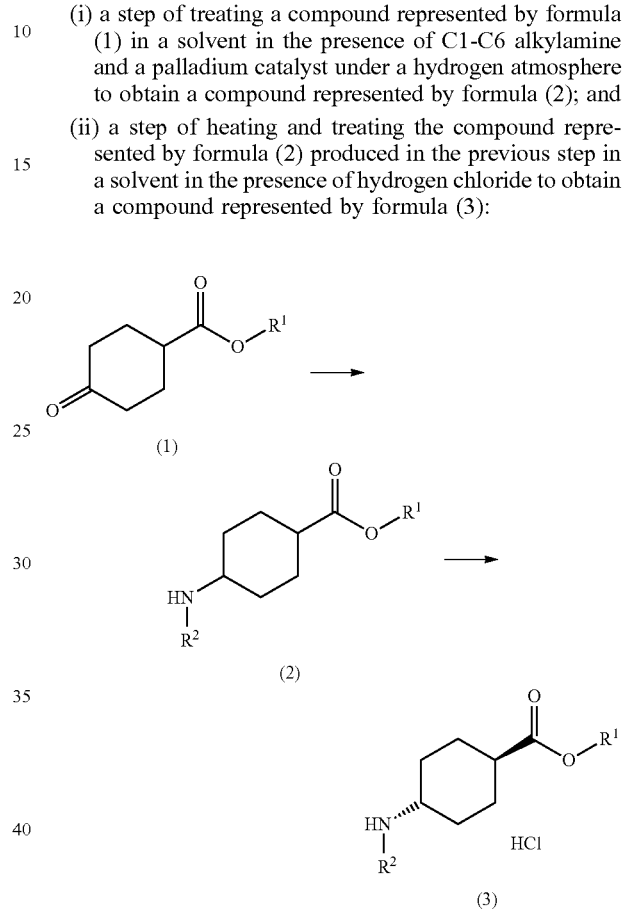

wherein $R^1$ represents a C1-C6 alkyl group and $R^2$ represents a C1-C6 alkyl group.

12. The method according to claim 11, wherein $R^1$ represents an ethyl group and $R^2$ represents an ethyl group.

13. The method according to claim 11, wherein in the step (i), the solvent is ethanol, the C1-C6 alkylamine is ethylamine, and the palladium catalyst is 5% palladium carbon.

14. The method according to claim 11, wherein in the step (ii), the solvent is xylene.

15. The method for producing a compound represented by formula (13) or a pharmacologically acceptable salt thereof according to claim 1, wherein a compound represented by formula (3) is produced by the method comprising:
   (i) a step of treating a compound represented by formula (1) in a solvent in the presence of C1-C6 alkylamine and a palladium catalyst under a hydrogen atmosphere to obtain a compound represented by formula (2); and
   (ii) a step of heating and treating the compound represented by formula (2) produced in the previous step in a solvent in the presence of hydrogen chloride to obtain a compound represented by formula (3):

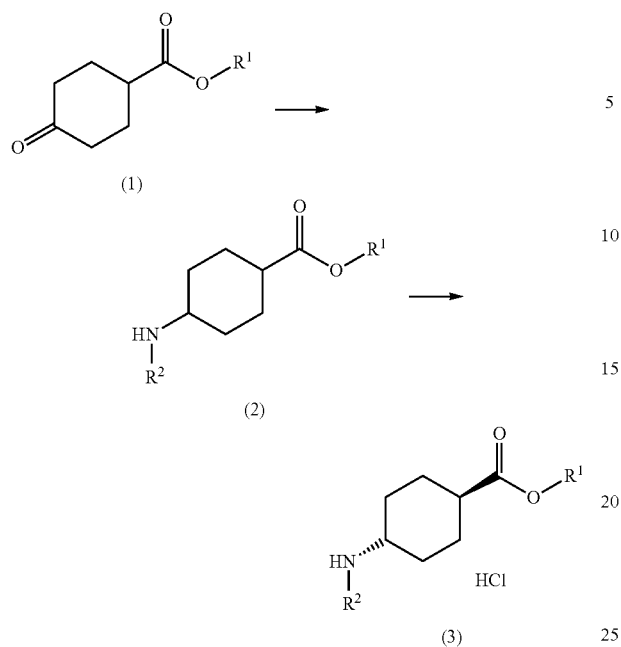
wherein $R^1$ represents a C1-C6 alkyl group and $R^2$ represents a C1-C6 alkyl group.
* * * * *